United States Patent
Yokoyama et al.

(10) Patent No.: US 8,748,014 B2
(45) Date of Patent: Jun. 10, 2014

(54) COMPOUND HAVING A SUBSTITUTED ANTHRACENE RING STRUCTURE AND PYRIDOINDOLE RING STRUCTURE, AND ORGANIC ELECTROLUMINESCENT DEVICE

(75) Inventors: Norimasa Yokoyama, Tsukuba (JP); Shuichi Hayashi, Tsukuba (JP); Kouki Kase, Tsukuba (JP); Hiroshi Ohkuma, Tsukuba (JP); Eiji Takahashi, Tsukuba (JP); Daizou Kanda, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 223 days.

(21) Appl. No.: 13/509,434

(22) PCT Filed: Nov. 10, 2010

(86) PCT No.: PCT/JP2010/070022
§ 371 (c)(1),
(2), (4) Date: May 11, 2012

(87) PCT Pub. No.: WO2011/059000
PCT Pub. Date: May 19, 2011

(65) Prior Publication Data
US 2012/0228598 A1    Sep. 13, 2012

(30) Foreign Application Priority Data
Nov. 12, 2009   (JP) .................. 2009-258613

(51) Int. Cl.
*H01L 51/54*  (2006.01)

(52) U.S. Cl.
USPC ........... 428/690; 428/917; 313/504; 313/505; 313/506; 257/40; 257/E51.05; 257/E51.026; 257/E51.032; 546/48; 546/79; 546/81; 546/101; 548/304.1; 548/418; 548/440; 544/234

(58) Field of Classification Search
USPC ............ 428/690, 917; 313/504, 505; 257/40, 257/E51.05, E51.026, E51.032; 546/18, 79, 546/81, 101; 548/304.1, 418, 440; 544/234
See application file for complete search history.

(56) References Cited

U.S. PATENT DOCUMENTS

| | | |
|---|---|---|
| 2007/0247063 A1 | 10/2007 | Murase et al. |
| 2009/0066226 A1 | 3/2009 | Sugita et al. |
| 2009/0174321 A1 | 7/2009 | Osaka et al. |
| 2009/0230857 A1* | 9/2009 | Choi et al. ................. 313/504 |
| 2009/0267498 A1 | 10/2009 | Kawakami et al. |
| 2011/0175079 A1 | 7/2011 | Yokoyama et al. |

FOREIGN PATENT DOCUMENTS

| | | |
|---|---|---|
| JP | 08 048656 | 2/1996 |
| JP | 2734341 | 3/1998 |
| JP | 3194657 | 7/2001 |
| JP | 2009 167175 | 7/2009 |
| WO | 03 060956 | 7/2003 |
| WO | 2005 113531 | 12/2005 |
| WO | 2006 114966 | 11/2006 |
| WO | 2009 063850 | 5/2009 |
| WO | 2009 099133 | 8/2009 |
| WO | 2009 131199 | 10/2009 |

OTHER PUBLICATIONS

International Search Report issued Dec. 7, 2010 in PCT/JP2010/070022 Filed Nov. 10, 2010.
U.S. Appl. No. 13/920,234, filed Jun. 18, 2013, Yokoyama, et al.

* cited by examiner

*Primary Examiner* — Gregory Clark
(74) *Attorney, Agent, or Firm* — Oblon, Spivak, McClelland, Maier & Neustadt, L.L.P.

(57) ABSTRACT

The present invention relates to a compound having a substituted anthracene ring structure and a pyridoindole ring structure, which is represented by the following general formula (1) or the following general formula (2); and an organic electroluminescent device having a pair of electrodes and at least one organic layer interposed therebetween, in which the compound having a substituted anthracene ring structure and a pyridoindole ring structure, which is represented by the following general formula (1) or the following general formula (2), is used as a constituent material of the aforementioned at least one organic layer.

[Chem. 1]

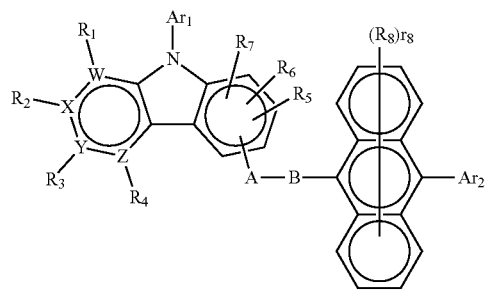

(1)

-continued

[Chem. 2]

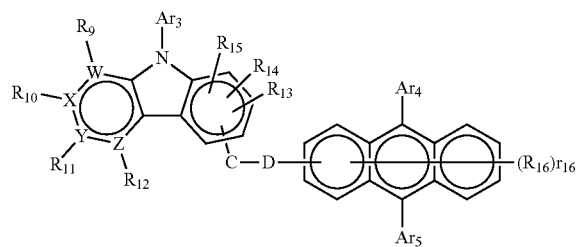

(2)

14 Claims, 4 Drawing Sheets

COMPOUND HAVING A SUBSTITUTED ANTHRACENE RING STRUCTURE AND PYRIDOINDOLE RING STRUCTURE, AND ORGANIC ELECTROLUMINESCENT DEVICE

TECHNICAL FIELD

The present invention relates to a compound suitable for an organic electroluminescent device which is a self-luminescent device suitable for various displaying devices, and the device. More specifically, it relates to a compound having a substituted anthracene ring structure and a pyridoindole ring structure, and to an organic electroluminescent device using the compound.

BACKGROUND ART

Since organic electroluminescent devices are self-luminescent devices, they are bright and excellent in visibility as compared with liquid-crystalline devices and capable of giving clear display, so that the organic electroluminescent devices have been actively studied.

In 1987, C. W. Tang et al. of Eastman Kodak Company put an organic electroluminescent device using organic materials into practical use by developing a device having a multilayered structure wherein various roles are assigned to respective materials. In particular, they formed a lamination of a fluorescent material capable of transporting electrons and an organic material capable of transporting holes, so that both charges are injected into the layer of the fluorescent material to emit light, thereby achieving a high luminance of 1,000 $cd/m^2$ or more at a voltage of 10 V or lower (see e.g., Patent Documents 1 and 2).

To date, many improvements have been performed for practical utilization of the organic electroluminescent devices, and high efficiency and durability have been achieved by an electroluminescent device wherein an anode, a hole-injection layer, a hole-transport layer, a light-emitting layer, an electron-transport layer, an electron-injection layer, and a cathode are sequentially provided on a substrate, to further segmentalize various roles (see e.g., Non-Patent Document 1).

Moreover, for the purpose of further improvement of luminous efficiency, utilization of triplet exciton has been attempted and utilization of a phosphorescent material has been investigated (see e.g., Non-Patent Document 2).

The light-emitting layer can be also prepared by doping a charge-transport compound, generally called a host material, with a fluorescent material or a phosphorescent material. As described in the above-mentioned Non-Patent Documents 1 and 2, the choice of the organic materials in organic electroluminescent devices remarkably affects various properties such as efficiency and durability of the devices.

In the organic electroluminescent devices, the charges injected from the both electrode are recombined in the light-emitting layer to attain light emission. However, since the mobility of holes is higher than the mobility of electrons, a problem of reduction in efficiency caused by a part of the holes passing through the light-emitting layer arises. Therefore, it is required to develop an electron-transport material in which the mobility of electrons is high.

A representative light-emitting material, tris(8-hydroxyquinoline)aluminum (hereinafter referred to as $Alq_3$) is commonly used also as an electron-transport material. However, since the mobility of electrons in the material is low and the material has a work function of 5.6 eV, it cannot be considered that the material has enough hole-blocking capability.

As a technique to prevent the passing of a part of holes through the light-emitting layer and to improve probability of charge recombination in the light-emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (e.g., bis(2-methyl-8-qunolinolate)-4-phenylphenolato aluminum (III) (hereinafter, referred to as BAlq)) (see e.g., Non-Patent Document 2), and the like.

On the other hand, as an electron-transport material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).

Since TAZ has a work function as large as 6.6 eV and thus exhibits a high hole-blocking ability, it is used as an electron-transport hole-blocking layer to be laminated onto the cathode side of a fluorescence-emitting layer or phosphorescence-emitting layer prepared by vacuum deposition, coating or the like, and contributes to increase the efficiency of organic electroluminescent devices (see e.g., Non-Patent Document 3).

However, TAZ has a great problem of having low electron-transport property, and it is necessary to prepare an organic electroluminescent device in combination with an electron-transport material having a higher electron-transport performance (see e.g., Non-Patent Document 4).

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in thin-film stability or are insufficient in the function of blocking holes. In order to improve device characteristics of the organic electroluminescent devices, it is desired to develop an organic compound which is excellent in electron-injection/transport performances and hole-blocking ability and is highly stable in thin-film state.

As a compound in which these characteristics have been improved, a compound having an anthracene ring structure and benzimidazole ring structure is proposed (see, e.g., Patent Document 4).

However, although devices where such compounds are used in electron injection layer and/or electron transport layer are improved in luminous efficiency or the like, it is not sufficient, and further lowering in driving voltage and enhancing in luminous efficiency, in particular, enhancing in current efficiency are required.

PRIOR ART DOCUMENTS

Patent Documents

Patent Document 1: JP-A-8-48656
Patent Document 2: Japanese Patent No. 3194657
Patent Document 3: Japanese Patent No. 2734341
Patent Document 4: WO 2003/060956

Non-Patent Document

Non-Patent Document 1: Japan Society of Applied Physics Ninth Workshop Preprint, pp. 55-61 (2001)
Non-Patent Document 2: Japan Society of Applied Physics Ninth Workshop Preprint, pp. 23-31 (2001)
Non-Patent Document 3: Fiftieth Meeting of Japan Society of Applied Physics and Related Societies, 28p-A-6 Lecture Preprint, p. 1413 (2003)
Non-Patent Document 4: Japan Society of Applied Physics, Journal of Organic Molecules/Bioelectronics Section, Vol. 11, No. 1, pp. 13-19 (2000)
Non-Patent Document 5: J. Chem. Soc., Perkin Trans. 1, 1505 (1999)
Non-Patent Document 6: J. Org. Chem., 60, 7508 (1995)
Non-Patent Document 7: Synth. Commun., 11, 513 (1981)

SUMMARY OF THE INVENTION

Problems to be Solved by the Invention

Objects of the present invention are to provide an organic compound having excellent properties, which is excellent in electron-injection/transport performances, has hole-blocking ability and has high stability in thin-film state, as a material for an organic electroluminescent device having a high efficiency and a high durability, and to provide an organic electroluminescent device having a high efficiency and a high durability using the compound.

As physical properties that the organic compound to be provided by the present invention is expected to have, there may be mentioned (1) good electron-injection performance, (2) high electron mobility, (3) excellent hole-blocking ability, (4) good stability in thin-film state, and (5) excellent thermal resistance. In addition, as physical properties that the organic electroluminescent device to be provided by the present invention is expected to have, there may be mentioned (1) high luminous efficiency and power efficiency, (2) low light emission initiation voltage, and (3) low practical driving voltage.

Means for Solving the Problems

Thus, in order to achieve the above objects, the present inventors have designed and chemically synthesized compounds having a substituted anthracene ring structure and a pyridoindole ring structure, with focusing on the fact that the pyridoindole ring structure has excellent electron-transport performance and is excellent in thermal resistance. The present inventors have experimentally produced various organic electroluminescent devices using the compounds, and have extensively performed property evaluation of the devices. As a result, they have accomplished the present invention.

That is, the present invention provides a compound having a substituted anthracene ring structure and a pyridoindole ring structure, which is represented by the following general formula (1) or the following general formula (2):

[Chem. 1]

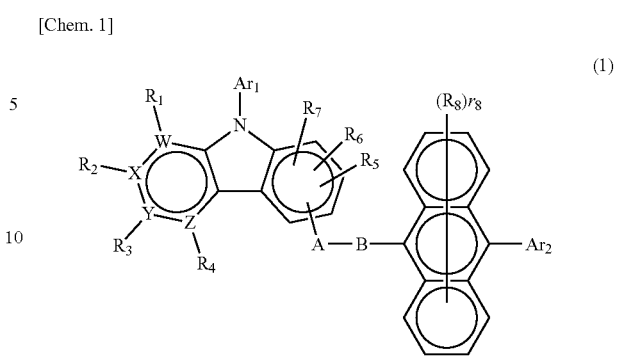

(1)

(In the formula, $Ar_1$ and $Ar_2$ may be the same or different from each other, wherein $Ar_1$ represents a substituted or unsubstituted aromatic hydrocarbon group, a substituted or unsubstituted aromatic heterocyclic group or a substituted or unsubstituted condensed polycyclic aromatic group, and $Ar_2$ represents a substituted or unsubstituted aromatic hydrocarbon group or a substituted or unsubstituted condensed polycyclic aromatic group; A and B may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_1$ to $R_7$ may be the same or different from one another, and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_8$ represents a deuterium atom, a fluorine atom, a chlorine atom, a cyano group, a trifluoromethyl group or a linear or branched alkyl group having from 1 to 6 carbon atoms; $r_8$ represents 0 or an integer of from 1 to 8, wherein when $r_8$ is 2 or more, two or more of $R_8$'s may be the same or different from one another and when $r_8$ is 0, it means no substitution with $R_8$; and each of W, X, Y and Z represents a carbon atom or a nitrogen atom, wherein only one of W, X, Y and Z is nitrogen atom and the nitrogen atom in that case does not have the hydrogen atom or substituent group of $R_1$ to $R_4$);

[Chem. 2]

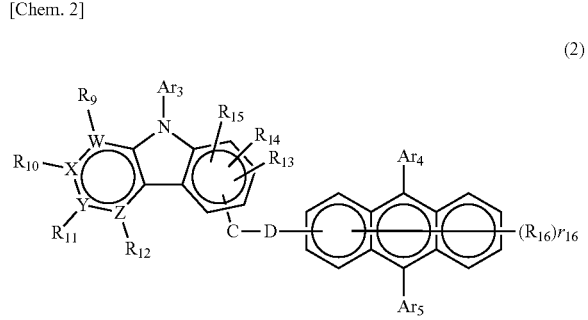

(2)

(In the formula, $Ar_3$, $Ar_4$ and $Ar_5$ may be the same or different from one another, wherein $Ar_3$ represents a substituted or unsubstituted aromatic hydrocarbon group, a substituted or unsubstituted aromatic heterocyclic group or a substituted or unsubstituted condensed polycyclic aromatic group, and each of $Ar_4$ and $Ar_5$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_9$ to $R_{15}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{16}$ represents a deuterium atom, a fluorine atom, a chlorine atom, a cyano group, a trifluoromethyl group or a linear or branched alkyl group having from 1 to 6 carbon atoms; $r_{16}$ represents 0 or an integer of from 1 to 7, wherein when $r_{16}$ is 2 or more, two or more of $R_{16}$'s may be the same or different from one another and when $r_{16}$ is 0, it means no substitution with $R_{16}$; and each of W, X, Y and Z represents a carbon atom or a nitrogen atom, wherein only one of W, X, Y and Z is nitrogen atom and the nitrogen atom in that case does not have the hydrogen atom or substituent group of $R_9$ to $R_{12}$).

Further, the present invention provides a compound having a substituted anthracene ring structure and a pyridoindole ring structure, which is represented by the following general formula (3):

[Chem. 3]

(3)

(In the formula, $Ar_6$ and $Ar_7$ may be the same or different from each other, wherein $Ar_6$ represents a substituted or unsubstituted aromatic hydrocarbon group, a substituted or unsubstituted aromatic heterocyclic group or a substituted or unsubstituted condensed polycyclic aromatic group, and $Ar_7$ represents a substituted or unsubstituted aromatic hydrocarbon group or a substituted or unsubstituted condensed polycyclic aromatic group; A and B may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{17}$ to $R_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{24}$ represents a deuterium atom, a fluorine atom, a chlorine atom, a cyano group, a trifluoromethyl group or a linear or branched alkyl group having from 1 to 6 carbon atoms; $r_{24}$ represents 0 or an integer of from 1 to 8, wherein when $r_{24}$ is 2 or more, two or more of $R_{24}$'s may be the same or different from one another and when $r_{24}$ is 0, it means no substitution with $R_{24}$; and each of W, X, Y and Z represents a carbon atom or a nitrogen atom, wherein only one of W, X, Y and Z is nitrogen atom and the nitrogen atom in that case does not have the hydrogen atom or substituent group of $R_{17}$ to $R_{20}$).

In the aforementioned general formula (3), it is preferred that each of A and B is a single bond, or A is a single bond and B is a phenylene group.

Further, the present invention provides a compound having a substituted anthracene ring structure and a pyridoindole ring structure, which is represented by the following general formula (3'):

[Chem. 4]

(3')

(In the formula, $Ar_6$ and $Ar_7$ may be the same or different from each other, wherein $Ar_6$ represents a substituted or unsubstituted aromatic hydrocarbon group, a substituted or unsubstituted aromatic heterocyclic group or a substituted or unsubstituted condensed polycyclic aromatic group, and $Ar_7$ represents a substituted or unsubstituted aromatic hydrocarbon group or a substituted or unsubstituted condensed polycyclic aromatic group; and $R_{17}$, $R_{18}$ and $R_{20}$ to $R_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

Further, the present invention provides a compound having a substituted anthracene ring structure and a pyridoindole ring structure, which is represented by the following general formula (3"):

[Chem. 5]

(3")

(In the formula, $Ar_6$ and $Ar_7$ may be the same or different from each other, wherein $Ar_6$ represents a substituted or unsubstituted aromatic hydrocarbon group, a substituted or unsubstituted aromatic heterocyclic group or a substituted or unsubstituted condensed polycyclic aromatic group, and $Ar_7$ represents a substituted or unsubstituted aromatic hydrocarbon group or a substituted or unsubstituted condensed polycyclic aromatic group; and $R_{17}$, $R_{18}$ and $R_{20}$ to $R_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

Further, the present invention provides a compound having a substituted anthracene ring structure and a pyridoindole ring structure, which is represented by the following general formula (4):

[Chem. 6]

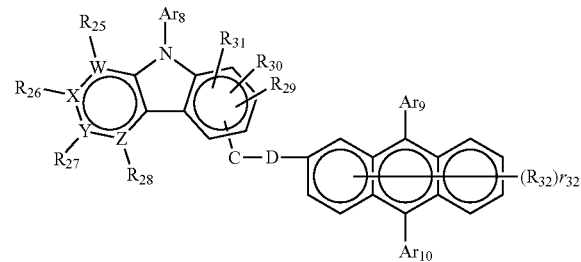

(4)

(In the formula, $Ar_8$, $Ar_9$ and $Ar_{10}$ may be the same or different from one another, wherein $Ar_8$ represents a substituted or unsubstituted aromatic hydrocarbon group, a substituted or unsubstituted aromatic heterocyclic group or a substituted or unsubstituted condensed polycyclic aromatic group, and each of $Ar_9$ and $Ar_{10}$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{25}$ to $R_{31}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{32}$ represents a deuterium atom, a fluorine atom, a chlorine atom, a cyano group, a trifluoromethyl group or a linear or branched alkyl group having from 1 to 6 carbon atoms; $r_{32}$ represents 0 or an integer of from 1 to 7, wherein when $r_{32}$ is 2 or more, two or more of $R_{32}$'s may be the same or different from one another and when $r_{32}$ is 0, it means no substitution with $R_{32}$; and each of W, X, Y and Z represents a carbon atom or a nitrogen atom, wherein only one of W, X, Y and Z is nitrogen atom and the nitrogen atom in that case does not have the hydrogen atom or substituent group of $R_{25}$ to $R_{28}$).

Further, the present invention provides a compound having a substituted anthracene ring structure and a pyridoindole ring structure, which is represented by the following general formula (5):

[Chem. 7]

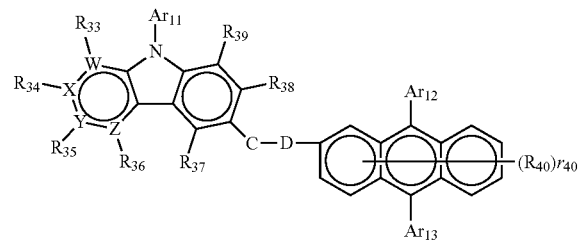

(5)

(In the formula, $Ar_{11}$, $Ar_{12}$ and $Ar_{13}$ may be the same or different from one another, wherein $Ar_{11}$ represents a substituted or unsubstituted aromatic hydrocarbon group, a substituted or unsubstituted aromatic heterocyclic group or a substituted or unsubstituted condensed polycyclic aromatic group, and each of $Ar_{12}$ and $Ar_{13}$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{33}$ to $R_{39}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{40}$ represents a deuterium atom, a fluorine atom, a chlorine atom, a cyano group, a trifluoromethyl group or a linear or branched alkyl group having from 1 to 6 carbon atoms; $r_{40}$ represents 0 or an integer of from 1 to 7, wherein when $r_{40}$ is 2 or more, two or more of $R_{40}$'s may be the same or different from one another and when $r_{40}$ is 0, it means no substitution with $R_{40}$; and each of W, X, Y and Z represents a carbon atom or a nitrogen atom, wherein only one of W, X, Y and Z is nitrogen atom and the nitrogen atom in that case does not have the hydrogen atom or substituent group of $R_{33}$ to $R_{36}$).

In the aforementioned general formula (5), it is preferred that each of C and D is a single bond.

Further, the present invention provides a compound having a substituted anthracene ring structure and a pyridoindole ring structure, which is represented by the following general formula (5'):

[Chem. 8]

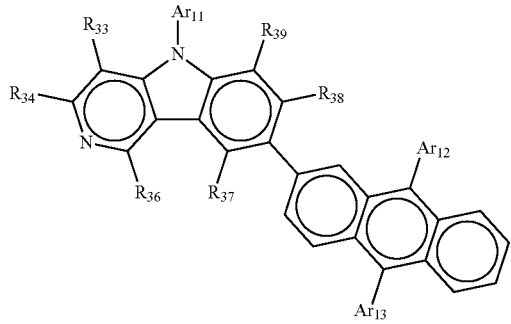

(5')

(In the formula, $Ar_{11}$, $Ar_{12}$ and $Ar_{13}$ may be the same or different from one another, wherein $Ar_{11}$ represents a substituted or unsubstituted aromatic hydrocarbon group, a substituted or unsubstituted aromatic heterocyclic group or a substituted or unsubstituted condensed polycyclic aromatic group, and each of $Ar_{12}$ and $Ar_{13}$ represents a substituted or unsubstituted aromatic hydrocarbon group or a substituted or unsubstituted condensed polycyclic aromatic group; and $R_{33}$, $R_{34}$ and $R_{36}$ to $R_{39}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

Further, the present invention provides an organic electroluminescent device having a pair of electrodes and at least one organic layer interposed therebetween, wherein the aforementioned at least one organic layer contains the compound having a substituted anthracene ring structure and a pyridoindole ring structure, which is represented by the general formula (1), general formula (2), general formula (3), general formula (3'), general formula (3''), general formula (4), general formula (5), or general formula (5').

The "aromatic hydrocarbon group", "aromatic heterocyclic group" or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group", represented by $Ar_1$, $Ar_3$, $Ar_6$, $Ar_8$, and $Ar_{11}$ in the general formulae (1) to (5), general formula (3'), general formula (3''), and general formula (5'), specifically includes a phenyl group, a biphenylyl group, a terphenylyl group, a tetrakisphenyl group, a styryl group, a naphthyl group, an anthryl group, an acenaphthenyl group, a phenanthryl group, a fluorenyl group, an indenyl group, a pyrenyl group, a pyridyl group, a triazyl group, a pyrimidyl group, a furanyl group, a pyronil group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group and an acridinyl group.

The "substituent" in the "substituted aromatic hydrocarbon group", "substituted aromatic heterocyclic group", or "substituted condensed polycyclic aromatic group", represented by $Ar_1$, $Ar_3$, $Ar_6$, $Ar_8$, and $Ar_{11}$ in the general formulae (1) to (5), general formula (3'), general formula (3''), and general formula (5'), specifically includes a deuterium atom, a fluorine atom, a chlorine atom, a cyano group, a trifluoromethyl group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, a phenyl group, a naphthyl group, an anthryl group, a fluorenyl group, a styryl group, a pyridyl group, a pyridoindolyl group, a quinolyl group, and a benzothiazolyl group. These substituents may be further substituted.

The "aromatic hydrocarbon group" or "condensed polycyclic aromatic group" in the "substituted or unsubstituted aromatic hydrocarbon group" or "substituted or unsubstituted condensed polycyclic aromatic group", represented by $Ar_2$, $Ar_4$, $Ar_5$, $Ar_7$, $Ar_9$, $Ar_{10}$, $Ar_{12}$, and $Ar_{13}$ in the general formulae (1) to (5), general formula (3'), general formula (3''), and general formula (5'), specifically includes a phenyl group, a biphenylyl group, a terphenylyl group, a naphthyl group, an anthryl group, a phenanthryl group, a fluorenyl group, an indenyl group, and a pyrenyl group.

The "substituent" in the "substituted aromatic hydrocarbon group" or "substituted condensed polycyclic aromatic group", represented by $Ar_2$, $Ar_4$, $Ar_5$, $Ar_7$, $Ar_9$, $Ar_{10}$, $Ar_{12}$, and $Ar_{13}$ in the general formulae (1) to (5), general formula (3'), general formula (3''), and general formula (5'), specifically includes a deuterium atom, a fluorine atom, a chlorine atom, a cyano group, a trifluoromethyl group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, a phenyl group, a naphthyl group, an anthryl group, a fluorenyl group, a styryl group, a pyridyl group, a pyridoindolyl group, a quinolyl group, and a benzothiazolyl group. These substituents may be further substituted.

The "aromatic hydrocarbon group", "aromatic heterocyclic group" or "condensed polycyclic aromatic group", in the "substituted or unsubstituted aromatic hydrocarbon group", "substituted or unsubstituted aromatic heterocyclic group", or "substituted or unsubstituted condensed polycyclic aromatic group", represented by $R_1$ to $R_7$, $R_9$ to $R_{15}$, $R_{17}$ to $R_{23}$, $R_{25}$ to $R_{31}$, and $R_{33}$ to $R_{39}$, in the general formulae (1) to (5), general formula (3'), general formula (3''), and general formula (5'), specifically includes a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a triazyl group, a pyrimidyl group, a furanyl group, a pyronil group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group, an acridinyl group, and a pyridoindolyl group.

The "substituent" in the "substituted aromatic hydrocarbon group", "substituted aromatic heterocyclic group", or "substituted condensed polycyclic aromatic group", represented by $R_1$ to $R_7$, $R_9$ to $R_{15}$, $R_{17}$ to $R_{23}$, $R_{25}$ to $R_{31}$, and $R_{33}$ to $R_{39}$, in the general formulae (1) to (5), general formula (3'), general formula (3''), and general formula (5'), specifically includes a deuterium atom, a fluorine atom, a chlorine atom, a trifluoromethyl group, a linear or branched alkyl group having 1 to 6 carbon atoms, a phenyl group, a biphenylyl group, a terphenylyl group, a tetrakisphenyl group, a styryl group, a naphthyl group, a fluorenyl group, phenanthryl group, an indenyl group, a pyrenyl group, and a pyridoindolyl group. These substituents may be further substituted.

The "linear or branched alkyl group having 1 to 6 carbon atoms", represented by $R_1$ to $R_{40}$ in the general formulae (1) to (5), the general formula (3'), the general formula (3''), and the general formula (5'), specifically includes a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, and a t-hexyl group.

The "aromatic hydrocarbon divalent group", "aromatic heterocyclic divalent group" or "condensed polycyclic aromatic divalent group", in the "substituted or unsubstituted aromatic hydrocarbon divalent group", "substituted or unsubstituted aromatic heterocyclic divalent group" or "substituted or unsubstituted condensed polycyclic aromatic divalent group", represented by A, B, C, and D in the general formulae (1) to (5), specifically includes a phenylene group, a biphenylylene group, a terphenylylene group, a tetrakisphenylene group, a naphthylene, an anthrylene group, a phenanthrylene group, a fluorenylene group, a phenanthrolylene group, an indenylene group, a pyrenylene group, a pyridinylene group, a pyrimidinylene group, a quinolylene group, a isoquinolylene group, an indolylene group, a carbazolylene group, a quinoxalinylene group, a benzimidazolylene group, a pyrazolylene group, a naphthyridinylene group, a phenanthrolinylene group, and an acridinylene group.

The "substituent" in the "substituted aromatic hydrocarbon divalent group", "substituted aromatic heterocyclic divalent group" or "substituted condensed polycyclic aromatic divalent group", represented by A, B, C, and D in the general formulae (1) to (5), specifically includes a deuterium atom, a fluorine atom, a chlorine atom, a cyano group, a trifluoromethyl group, a linear or branched alkyl group having 1 to 6 carbon atoms, a phenyl group, a biphenyl group, a terphenyl group, a tetrakisphenyl group, a styryl group, a naphthyl group, a fluorenyl group, a phenanthryl group, an indenyl group, a pyrenyl group, and a pyridoindolyl group. These substituents may be further substituted.

The compound having a substituted anthracene ring structure and a pyridoindole ring structure, which is represented by the general formula (1) or general formula (2) of the present invention, is a novel compound, has high electron mobility as compared with conventional electron-transport materials, has excellent hole-blocking ability, can be present with thermal stability under high temperature condition, and is stable in thin-film state.

The compound having a substituted anthracene ring structure and a pyridoindole ring structure, which is represented by the general formula (1) or general formula (2) of the present invention, can be used as a constituent material for an electron-injection layer and/or an electron-transport layer of an organic electroluminescent device (hereinafter referred to as an "organic EL device"). The use of the material of the present invention, which is excellent in electron-injection/transport performances as compared with conventional materials, provides effects of an improvement in electron-transport efficiency from the electron-transport layer to the light-emitting layer to improve luminous efficiency as well as lowering in driving voltage to improve durability of the organic EL device.

The compound having a substituted anthracene ring structure and a pyridoindole ring structure, which is represented by the general formula (1) or general formula (2) of the present invention, can be also used as a constituent material for a hole-blocking layer of an organic EL device. The use of the material of the present invention, which is excellent in hole-blocking ability and electron-transport performance as compared with conventional materials and has high stability in thin-film, provides effects of lowering in driving voltage while maintaining high luminous efficiency and an improvement in current durability to improve maximum light-emission luminance of the organic EL device.

The compound having a substituted anthracene ring structure and a pyridoindole ring structure, which is represented by the general formula (1) or general formula (2) of the present invention, can be also used as a constituent material for a light-emitting layer of an organic EL device. The use of a light-emitting layer in which the material of the present invention, excellent in electron-transport performance as compared with conventional materials and having a wide band-gap, as a host material for the light-emitting layer, and by a fluorescent material or a phosphorescent material, called a dopant, is carried, provides an effect of realizing an organic EL device exhibiting a lowered driving voltage and having an improved luminous efficiency.

The organic EL device of the present invention employs the compound having a substituted anthracene ring structure and a pyridoindole ring structure, which compound exhibits high electron mobility as compared with conventional electron-transport materials, has excellent hole-blocking ability, can be present with thermal stability under high temperature condition, and is stable in thin-film state. Therefore, it becomes possible to realize high efficiency and high durability.

Effects of the Invention

The compound having a substituted anthracene ring structure and a pyridoindole ring structure is useful as a constituent material for an electron-injection layer, an electron-transport layer, a hole-blocking layer, or a light-emitting layer of an organic EL device, and the compound exhibits excellent hole-blocking ability, is stable in thin-film state, and has excellent thermal resistance. The organic EL device of the present invention exhibits high luminous efficiency and power efficiency, whereby the practical driving voltage of the device can be lowered. By lowering the light emission initiation voltage, the durability can be improved.

MODE FOR CARRYING OUT THE INVENTION

Figure 1:
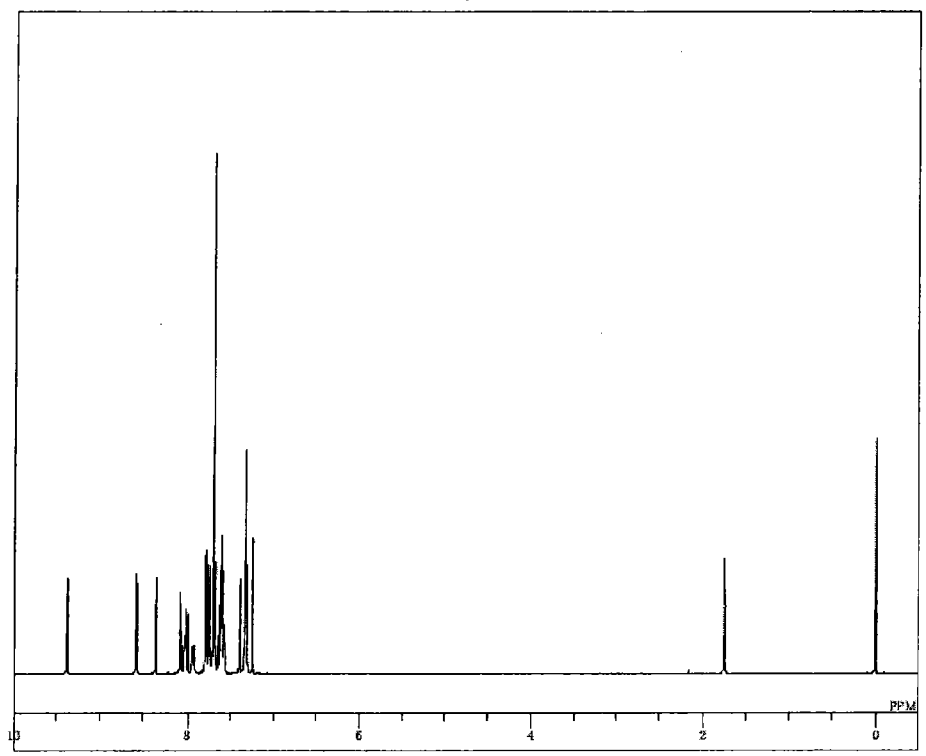
FIG. 1 is a 1H-NMR chart of the compound (Compound 10) of Invention Example 1.

The compound having the substituted anthracene ring structure and pyridoindole ring structure, which is represented by the general formula (1) or general formula (2) of the present invention, is a novel compound, and these compounds can be synthesized, for example, in the following manner. Firstly, by carrying out cyclization reaction of a corresponding halogenoanilinopyridine by a palladium catalyst to synthesize a corresponding pyridoindole derivative (see e.g., Non-Patent Document 5) and carrying out a condensation reaction such as Ullmann reaction or Buchwald-Hartwig reaction with various halide of aromatic hydrocarbon compounds, condensed polycyclic aromatic compounds or aromatic heterocyclic compounds, a pyridoindole derivative in which the corresponding 5-position is substituted with aryl group can be synthesized. By carrying out bromination of this pyridoindole derivative in which the corresponding 5-position is substituted with aryl group, with N-bromosuccinimide and the like, a corresponding bromo compound can be synthesized. By carrying out a cross coupling reaction such as Suzuki coupling (see e.g., Non-Patent Document 7) of this corresponding bromo compound with a boric acid or boric ester having anthracene ring structure synthesized by a conventional method (see e.g., Non-Patent Document 6), a compound having a substituted anthracene ring structure and a pyridoindole ring structure can be synthesized.

Among the compounds having a substituted anthracene ring structure and a pyridoindole ring structure, which is represented by the general formula (1) or general formula (2) of the present invention, illustrative examples of the preferred compounds are shown in the following, though the present invention is not limited to these compounds.

[Chem. 9]

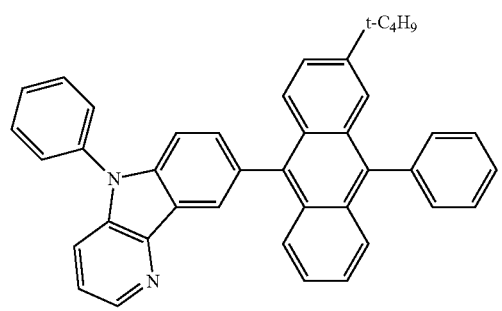

(Compound 6)

[Chem. 10]

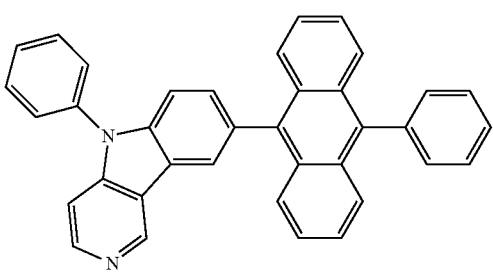

(Compound 7)

[Chem. 11]

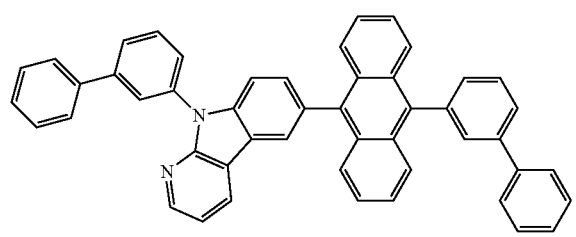

(Compound 8)

[Chem. 12]

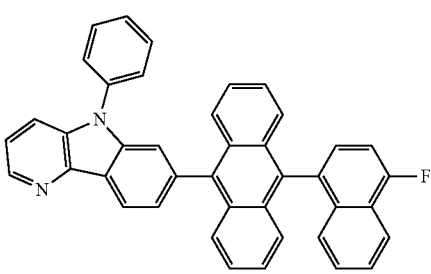

(Compound 9)

[Chem. 13]

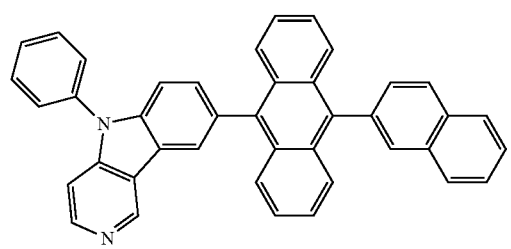

(Compound 10)

[Chem. 14]

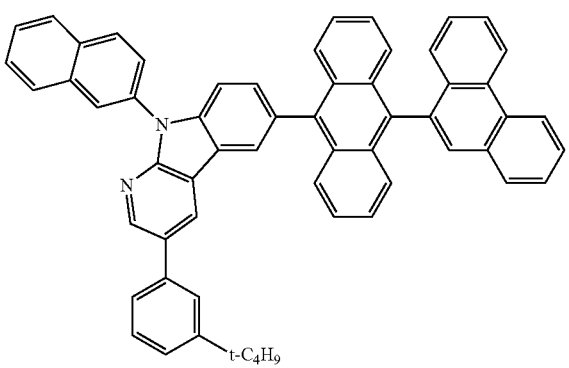

(Compound 11)

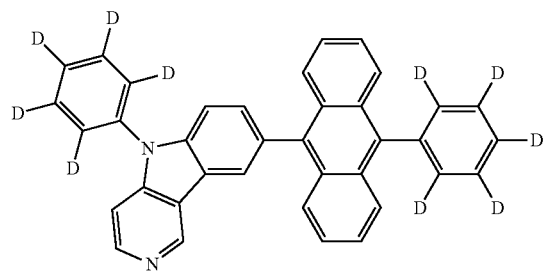
(Compound 12)
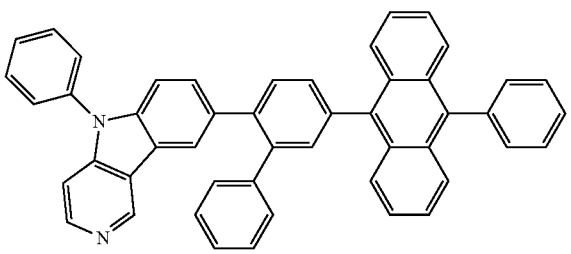
(Compound 13)
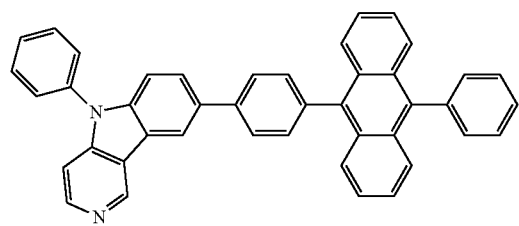
(Compound 14)
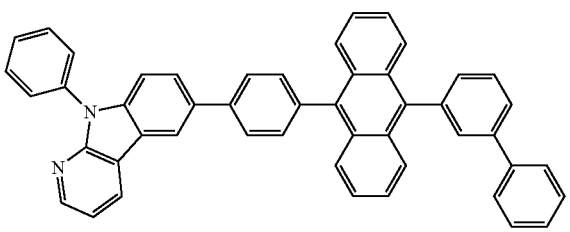
(Compound 15)
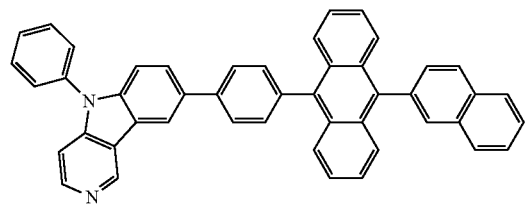
(Compound 16)
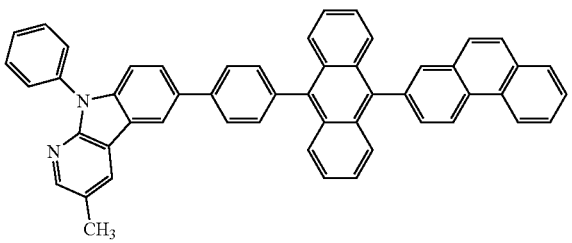
(Compound 17)
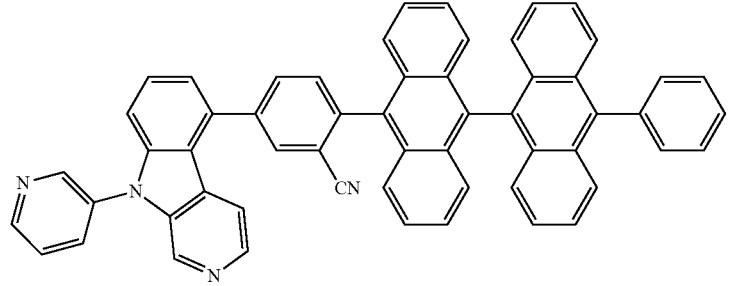
(Compound 18)
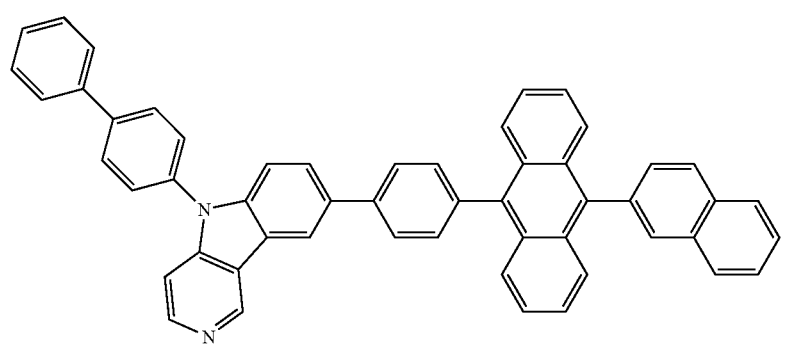
(Compound 19)

[Chem. 23]
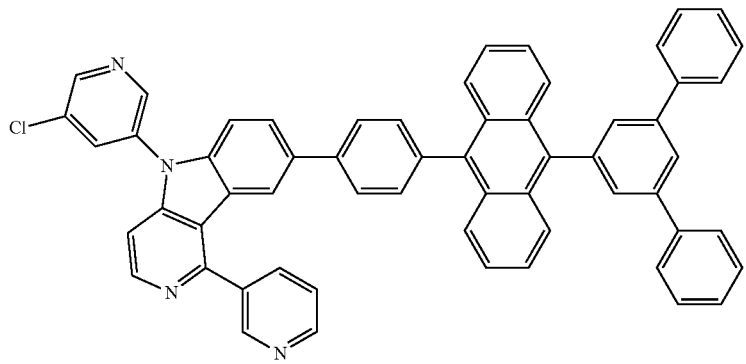
(Compound 20)
[Chem. 24]
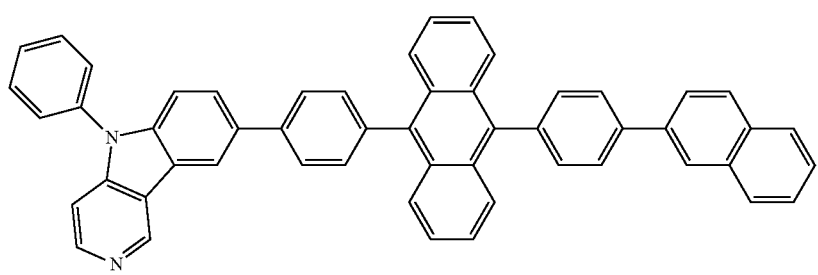
(Compound 21)
[Chem. 25]
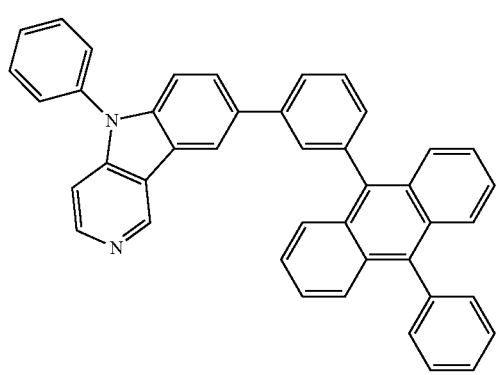
(Compound 22)
[Chem. 26]
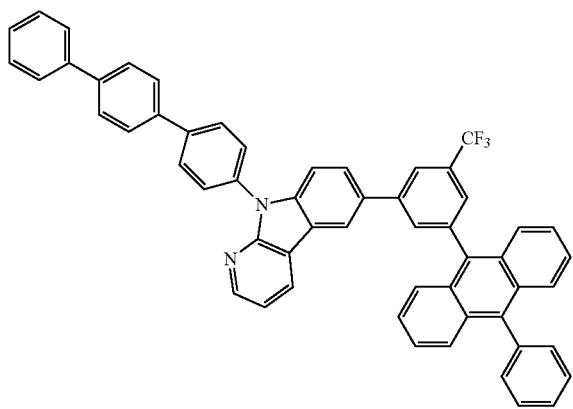
(Compound 23)
[Chem. 27]
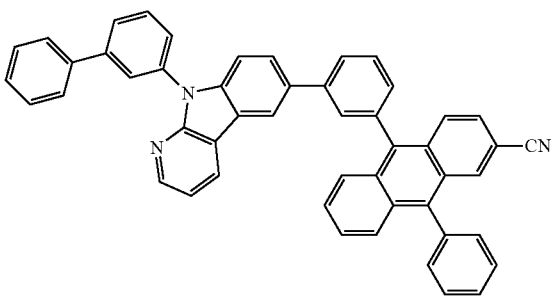
(Compound 24)

-continued
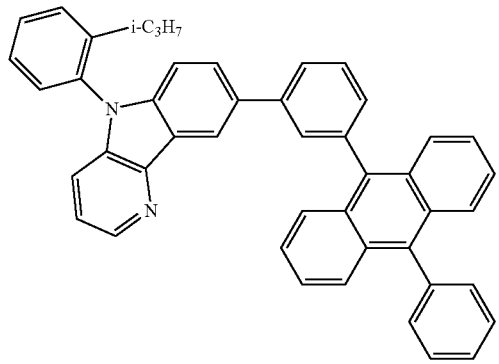
(Compound 25)
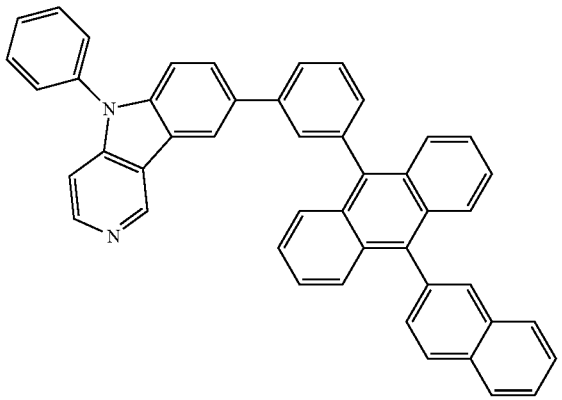
(Compound 26)
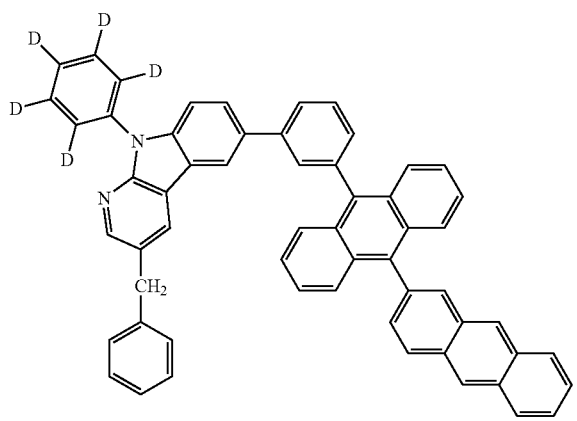
(Compound 27)
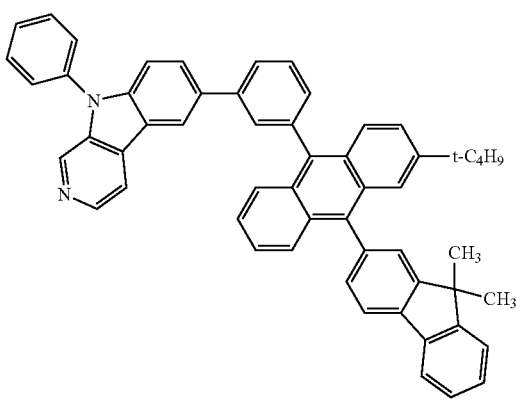
(Compound 28)
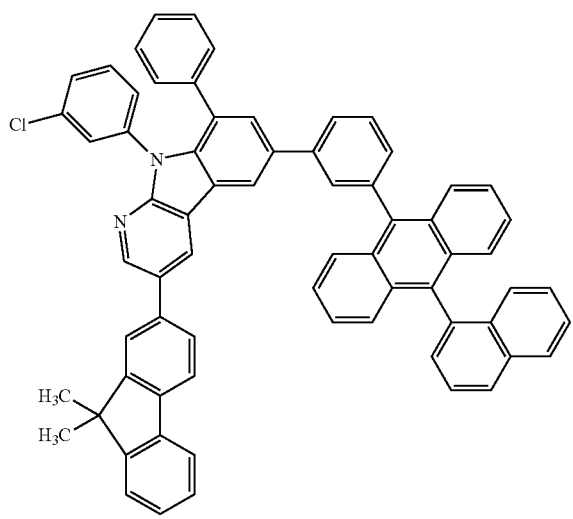
(Compound 29)
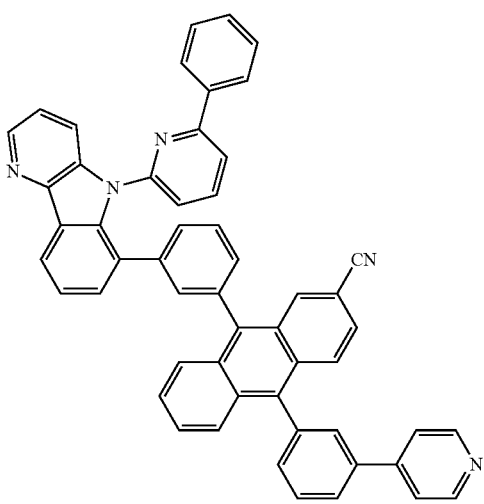
(Compound 30)

-continued
[Chem. 34]
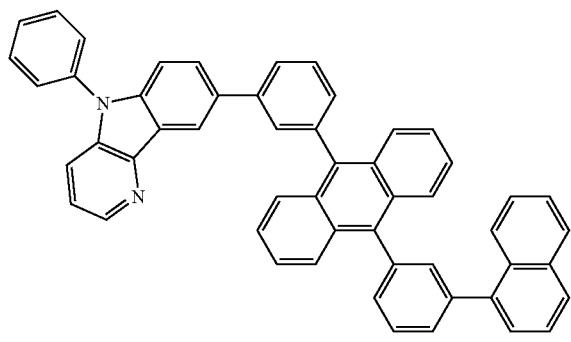
(Compound 31)
[Chem. 35]
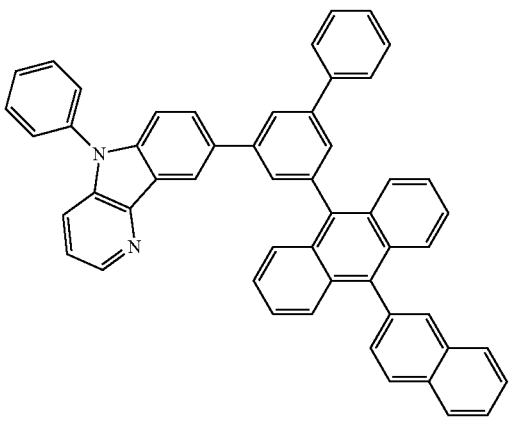
(Compound 32)
[Chem. 36]
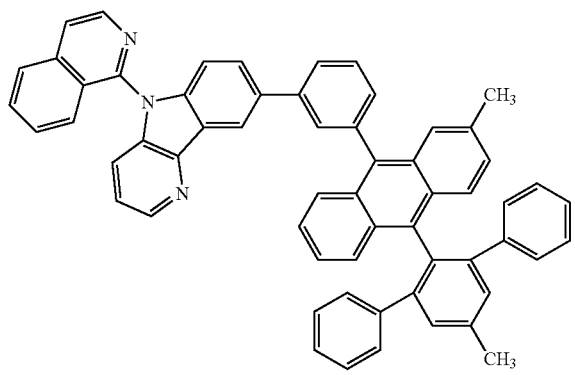
(Compound 33)
[Chem. 37]
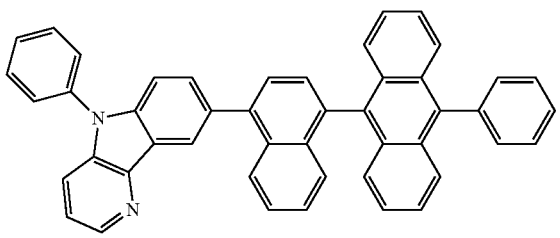
(Compound 34)
[Chem. 38]
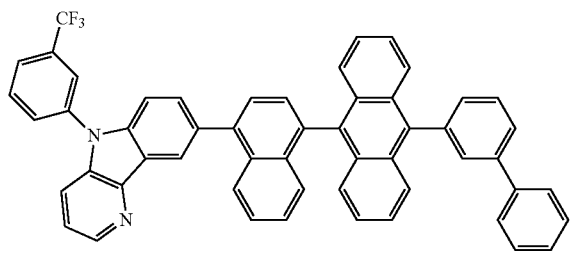
(Compound 35)
[Chem. 39]
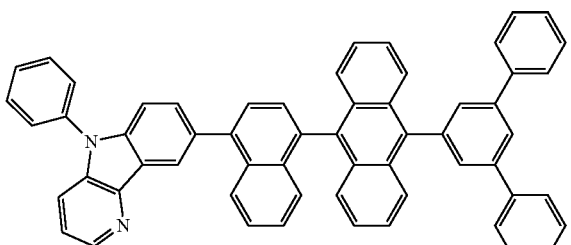
(Compound 36)
[Chem. 40]
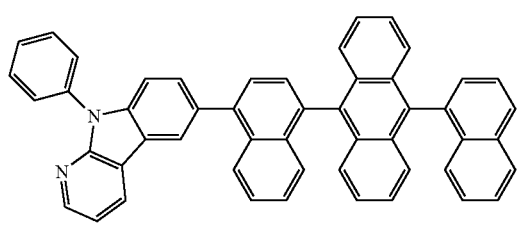
(Compound 37)
[Chem. 41]
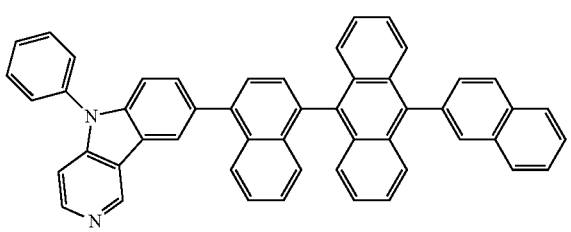
(Compound 38)

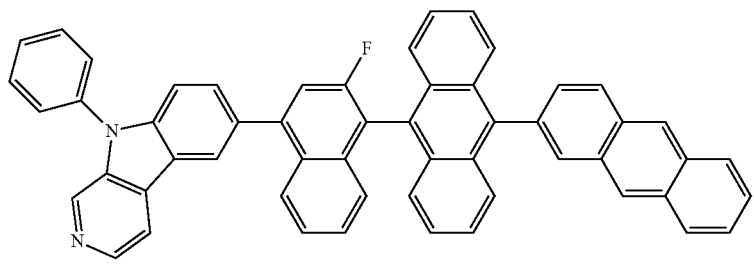
(Compound 39)
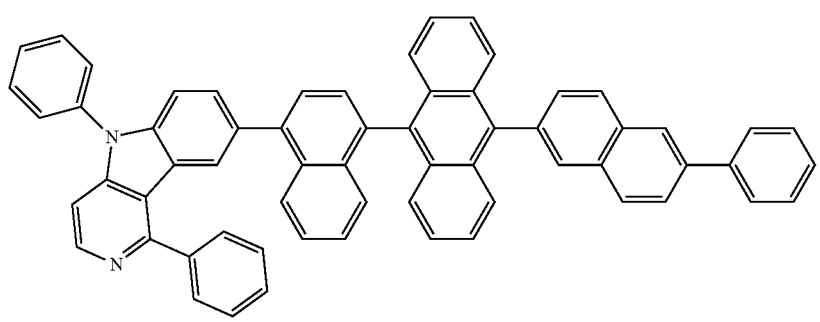
(Compound 40)
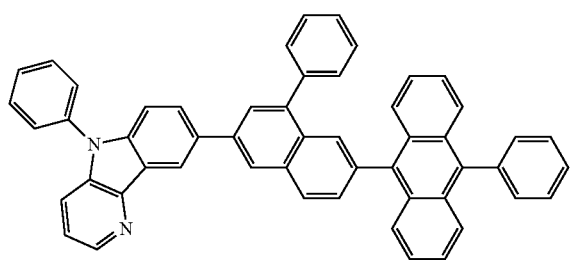
(Compound 41)
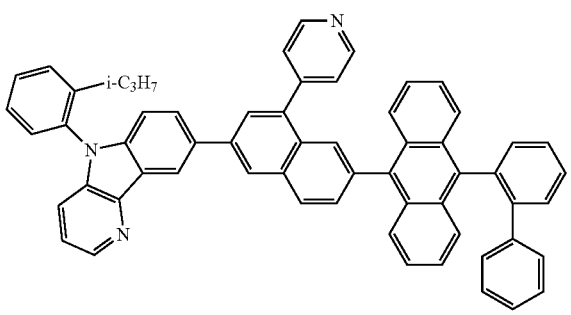
(Compound 42)
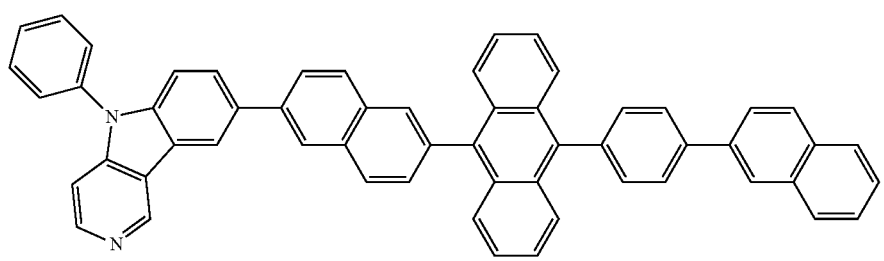
(Compound 43)
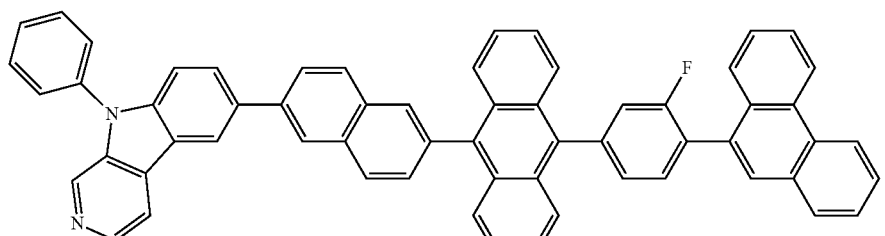
(Compound 44)

[Chem. 48]
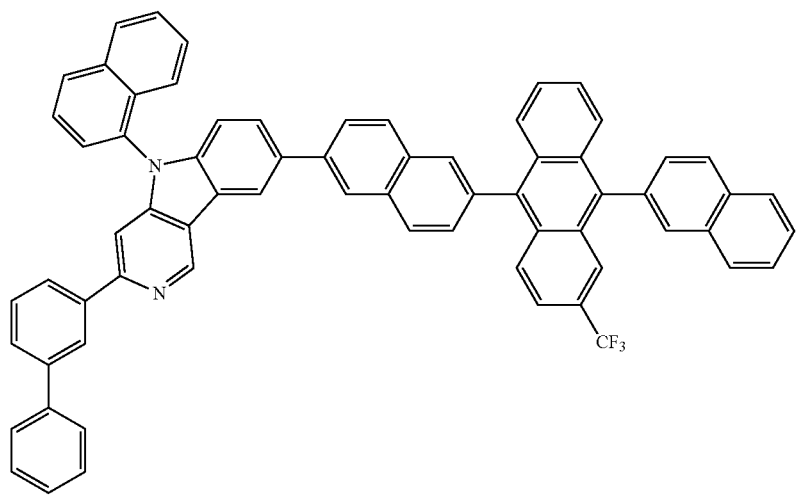
(Compound 45)
[Chem. 49]
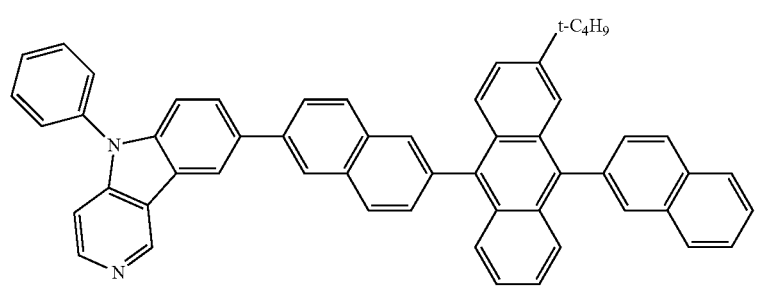
(Compound 46)
[Chem. 50]
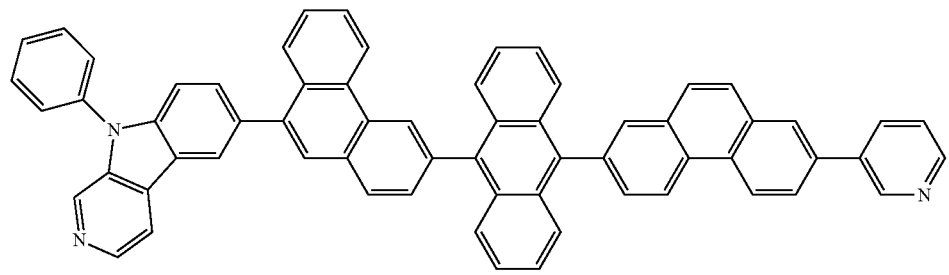
(Compound 47)
[Chem. 51]
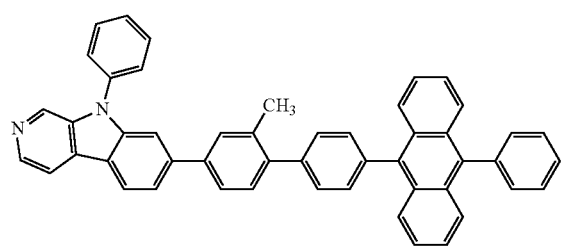
(Compound 48)
[Chem. 52]
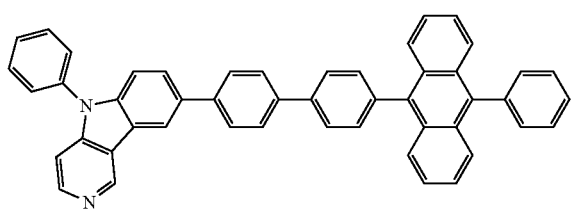
(Compound 49)

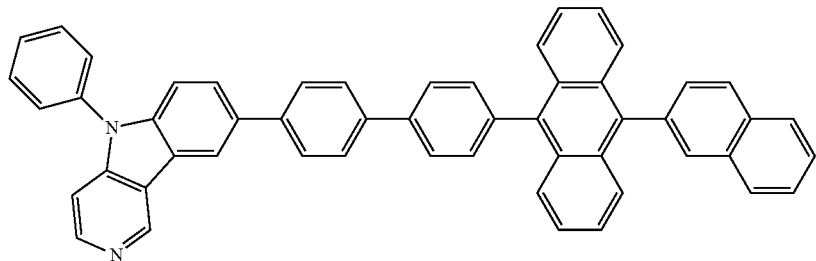
(Compound 50)
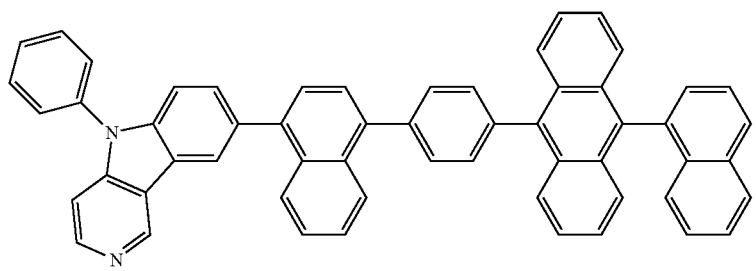
(Compound 51)
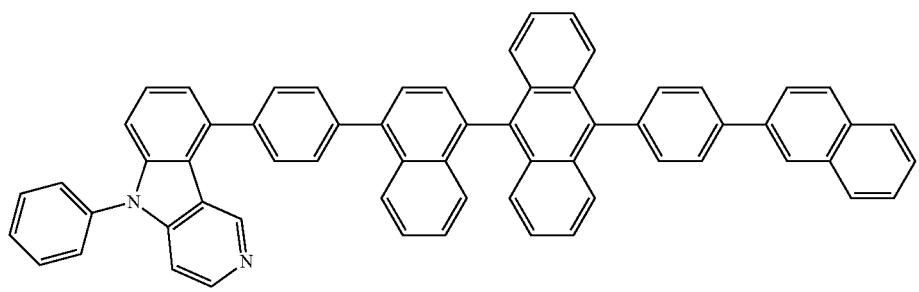
(Compound 52)
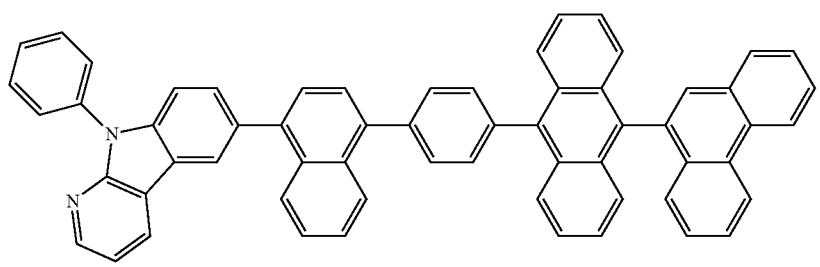
(Compound 53)
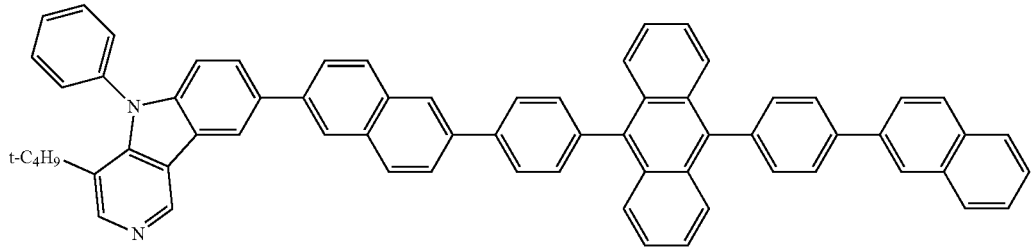
(Compound 54)

-continued
[Chem. 58]
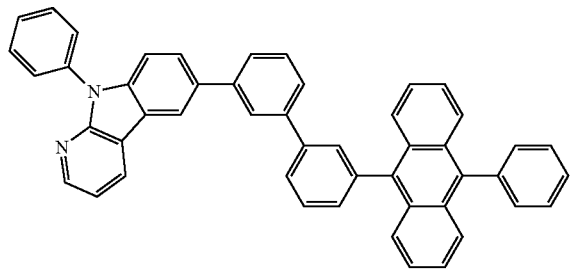
(Compound 55)
[Chem. 59]
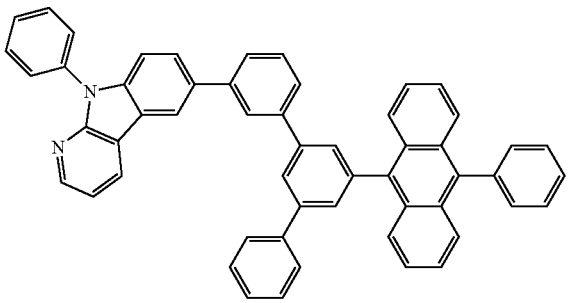
(Compound 56)
[Chem. 60]
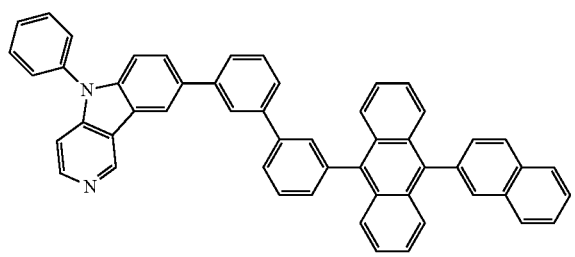
(Compound 57)
[Chem. 61]
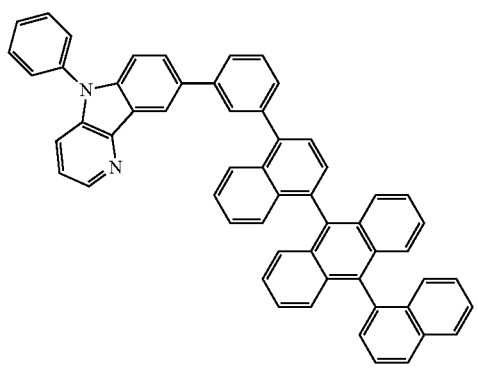
(Compound 58)
[Chem. 62]
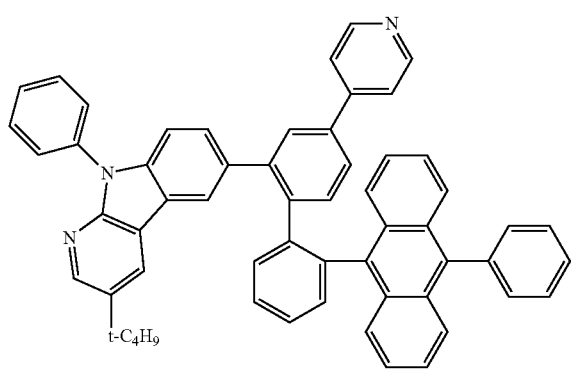
(Compound 59)
[Chem. 63]
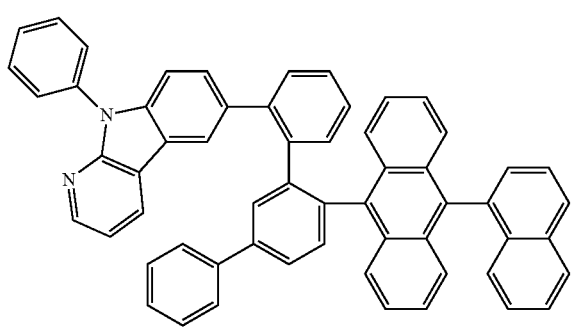
(Compound 60)

-continued
[Chem. 64]
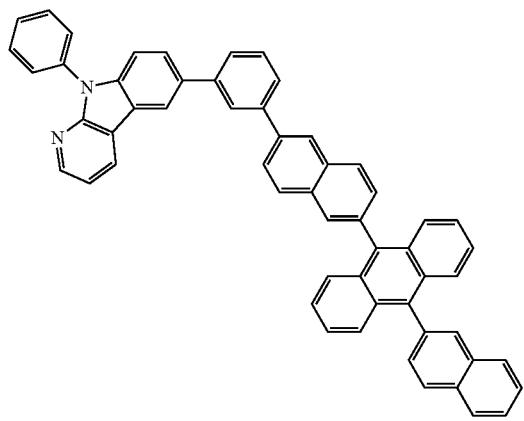
(Compound 61)
[Chem. 65]
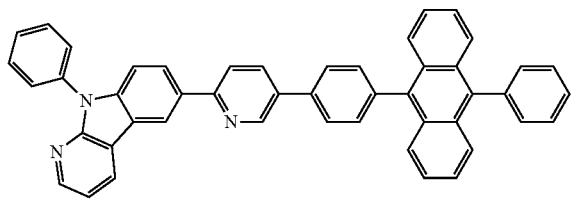
(Compound 62)
[Chem. 66]
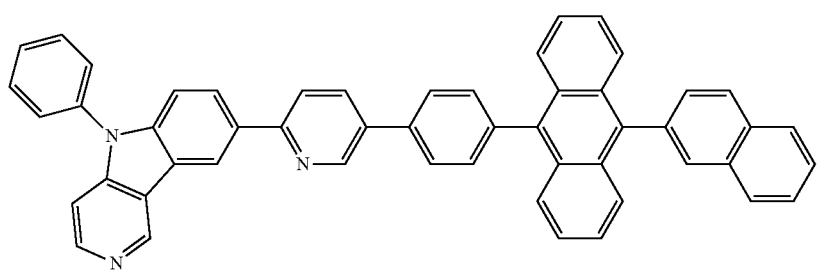
(Compound 63)
[Chem. 67]
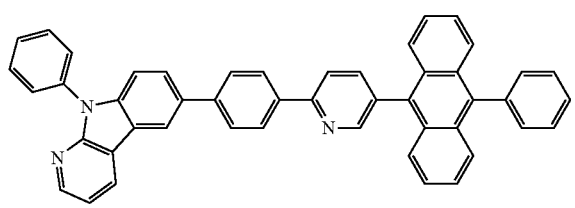
(Compound 64)
[Chem. 68]
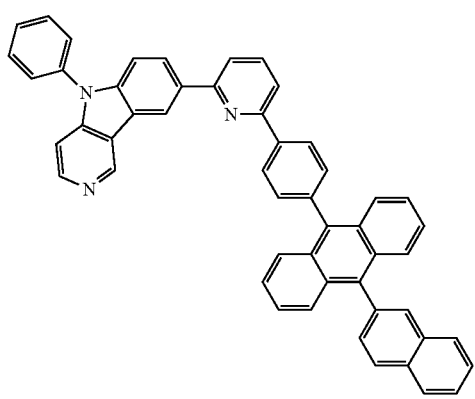
(Compound 65)
[Chem. 69]
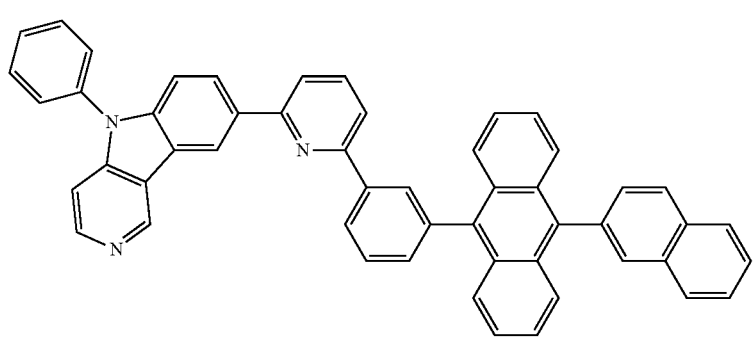
(Compound 66)

-continued
[Chem. 70]
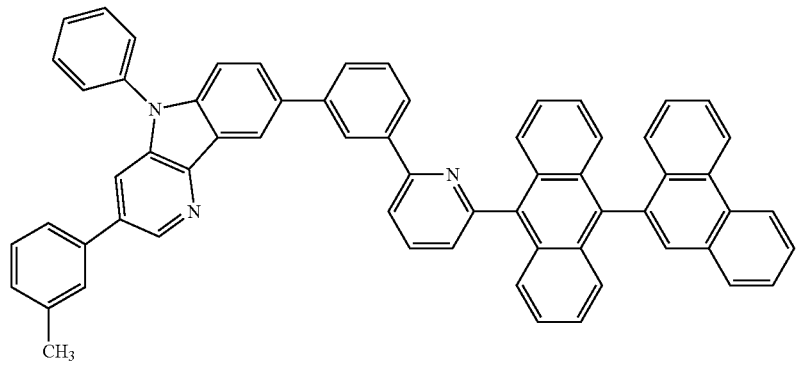
(Compound 67)
[Chem. 71]
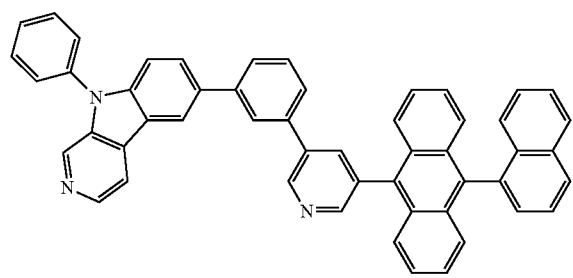
(Compound 68)
[Chem. 72]
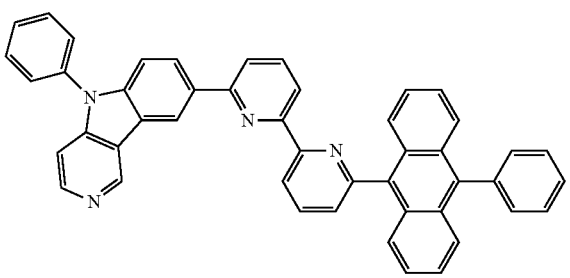
(Compound 69)
[Chem. 73]
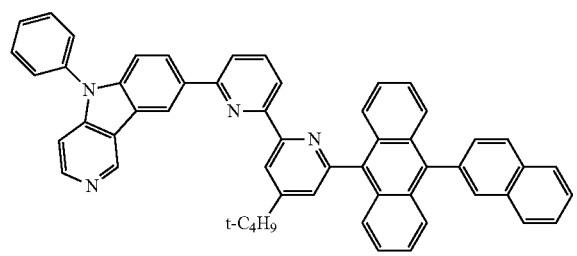
(Compound 70)
[Chem. 74]
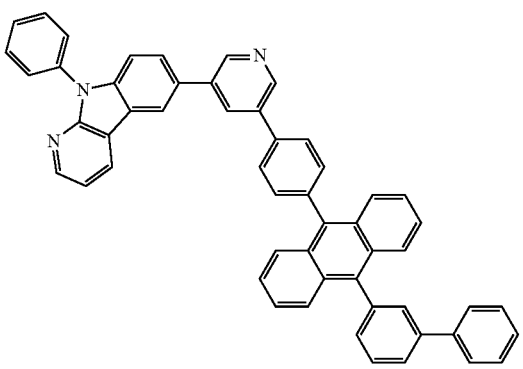
(Compound 71)
[Chem. 75]
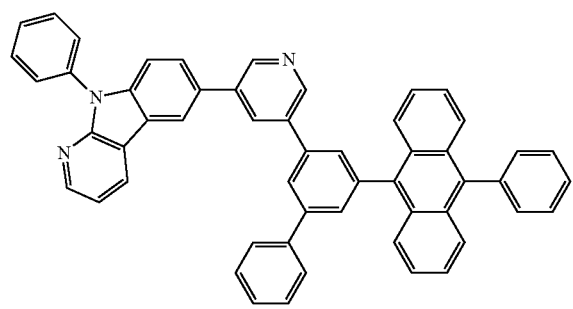
(Compound 72)
[Chem. 76]
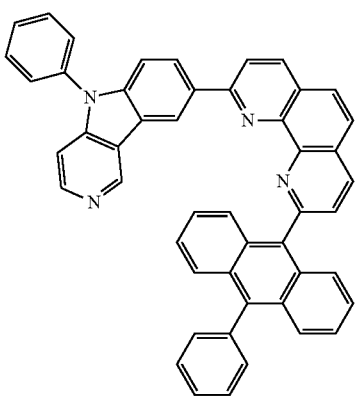
(Compound 73)

[Chem. 77]
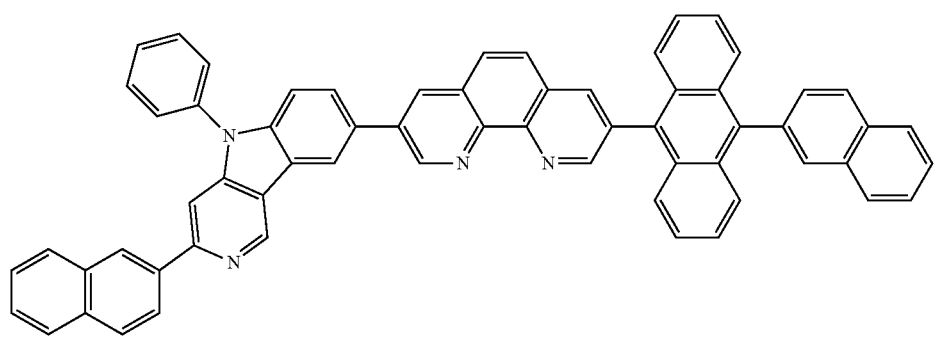
(Compound 74)
[Chem. 78]
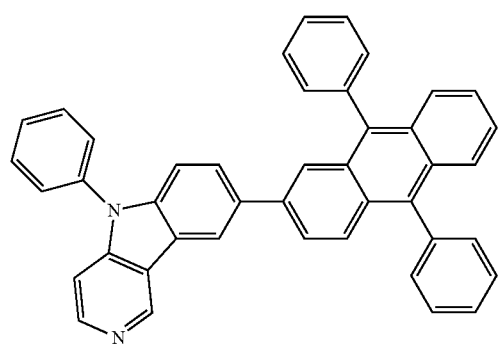
(Compound 75)
[Chem. 79]
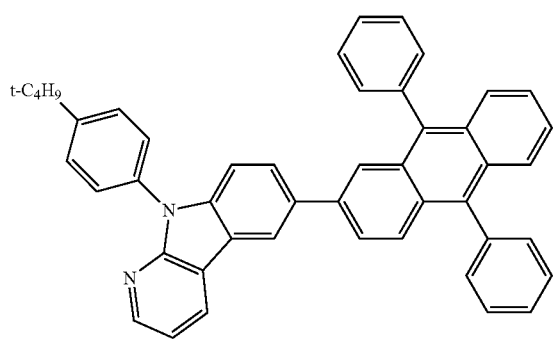
(Compound 76)
[Chem. 80]
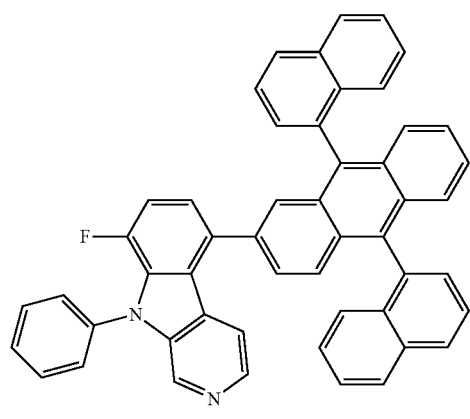
(Compound 77)
[Chem. 81]
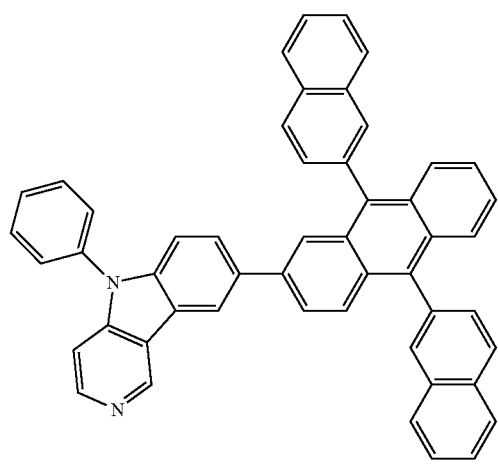
(Compound 78)

[Chem. 82]
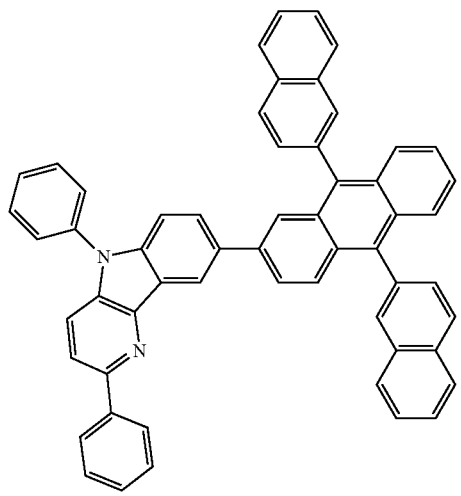
(Compound 79)
[Chem. 83]
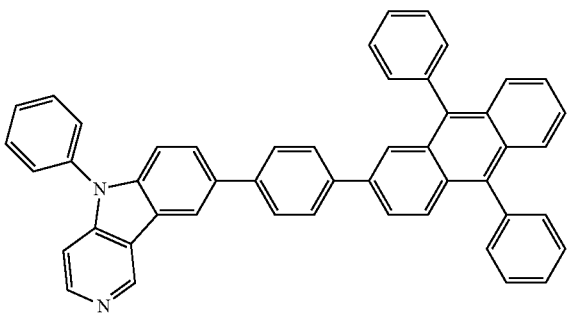
(Compound 80)
[Chem. 84]
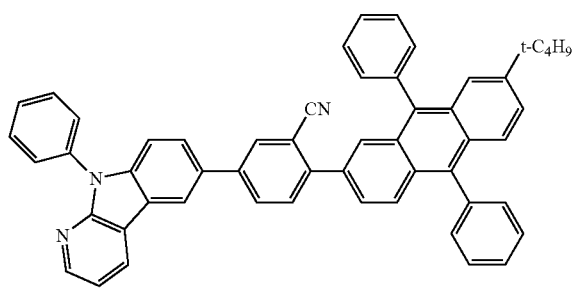
(Compound 81)
[Chem. 85]
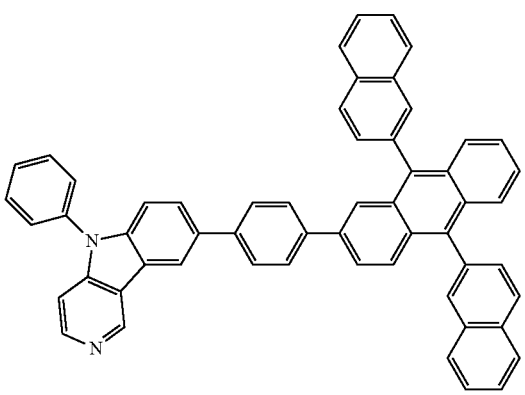
(Compound 82)
[Chem. 86]
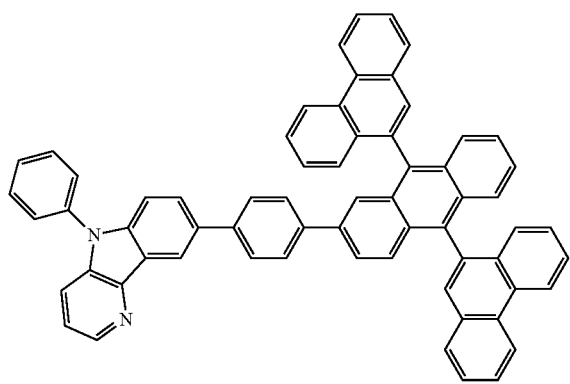
(Compound 83)
[Chem. 87]
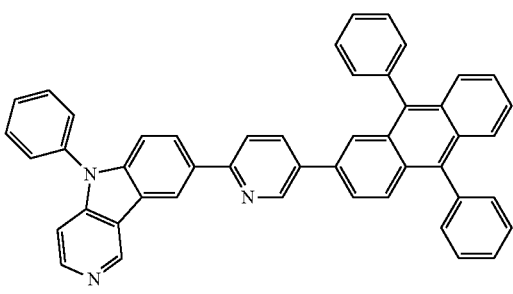
(Compound 84)

-continued
[Chem. 88]
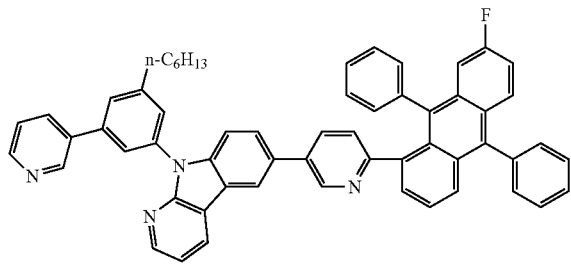
(Compound 85)
[Chem. 89]
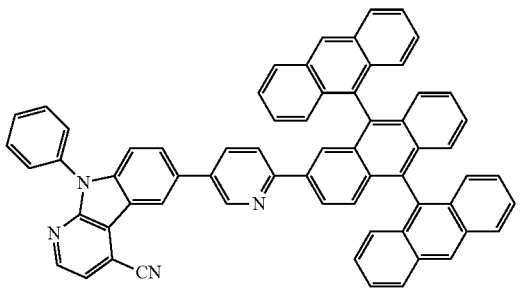
(Compound 86)
[Chem. 90]
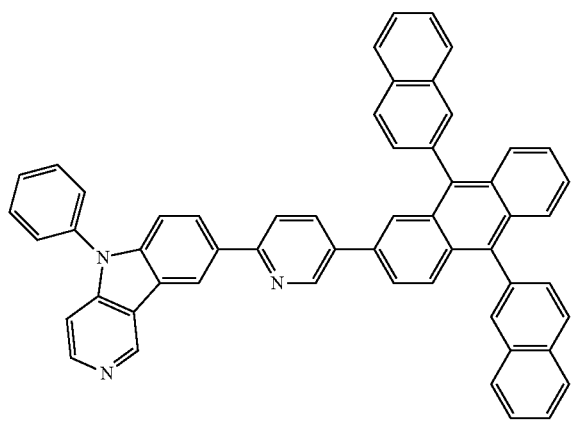
(Compound 87)
[Chem. 91]
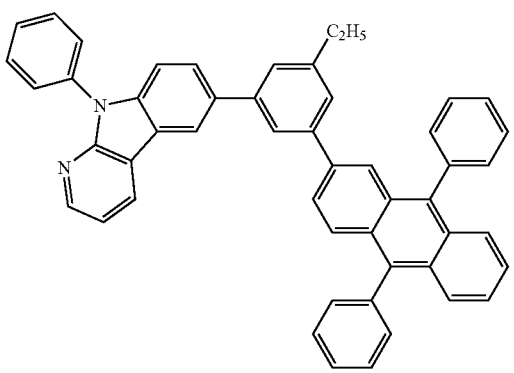
(Compound 88)
[Chem. 92]
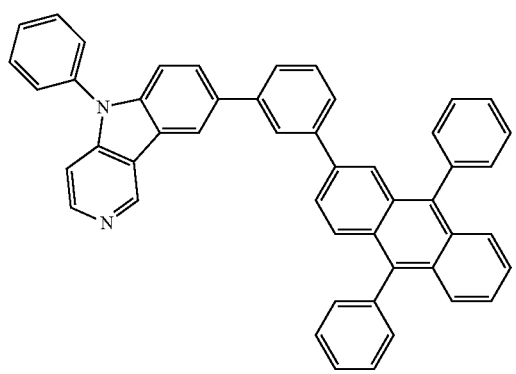
(Compound 89)
[Chem. 93]
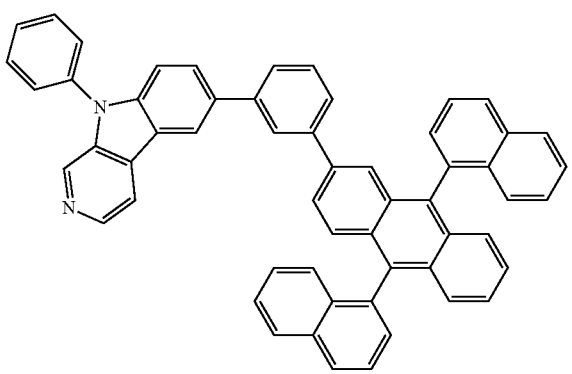
(Compound 90)

-continued
[Chem. 94]
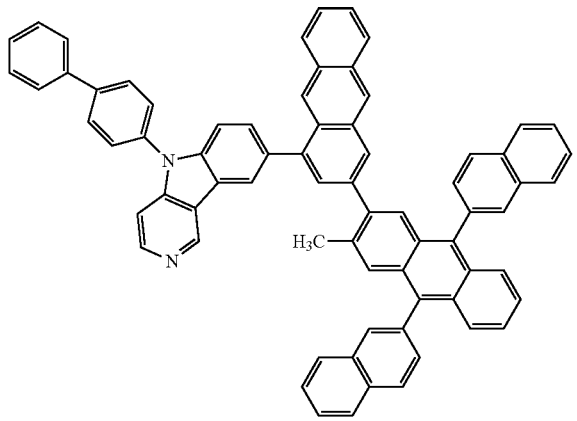
(Compound 91)
[Chem. 95]
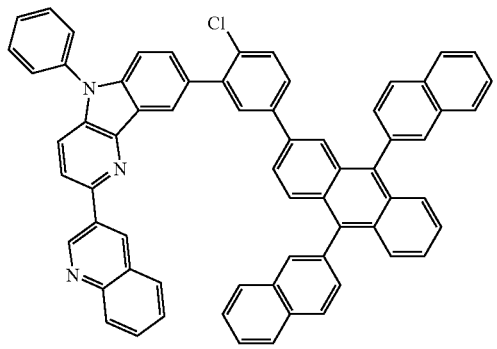
(Compound 92)
[Chem. 96]
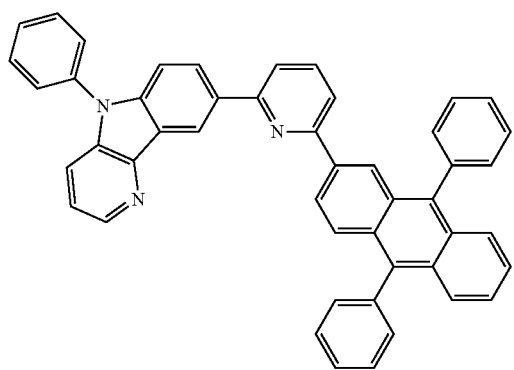
(Compound 93)
[Chem. 97]
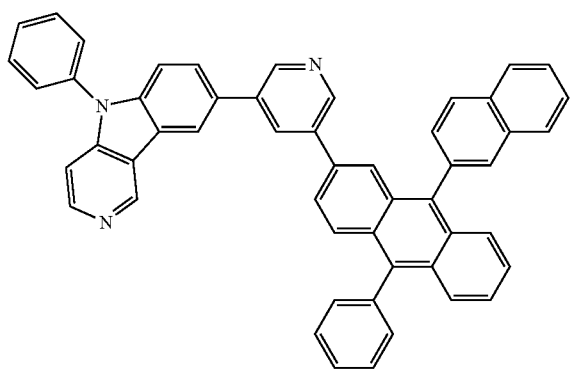
(Compound 94)
[Chem. 98]
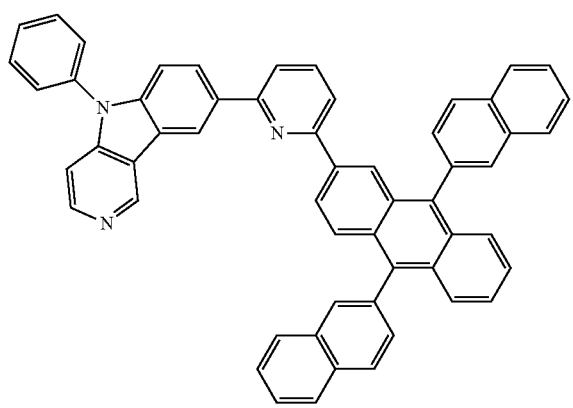
(Compound 95)
[Chem. 99]
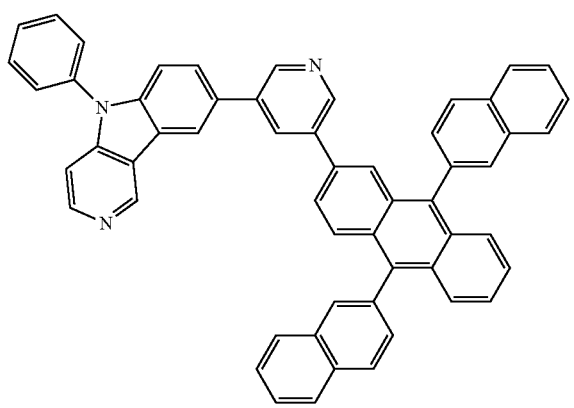
(Compound 96)

[Chem. 100]
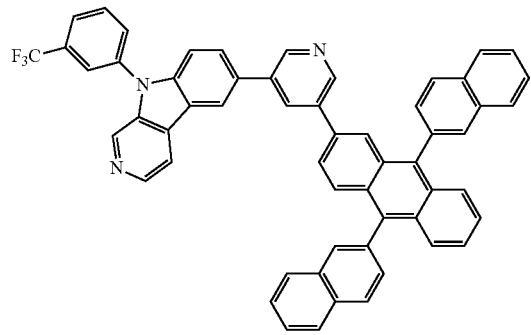
(Compound 97)
[Chem. 101]
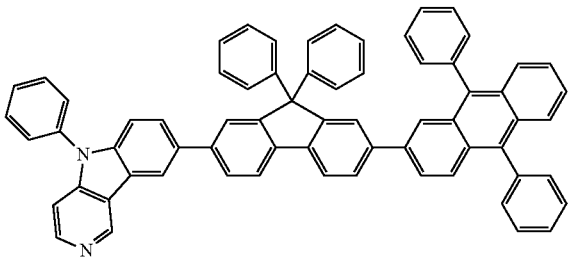
(Compound 98)
[Chem. 102]
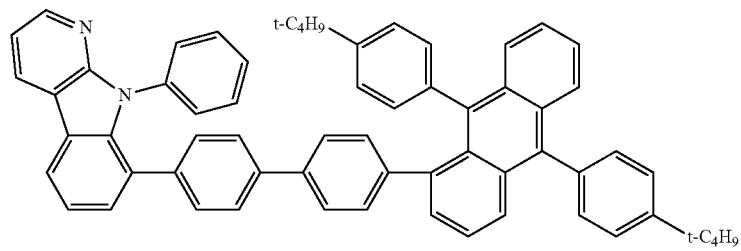
(Compound 99)
[Chem. 103]
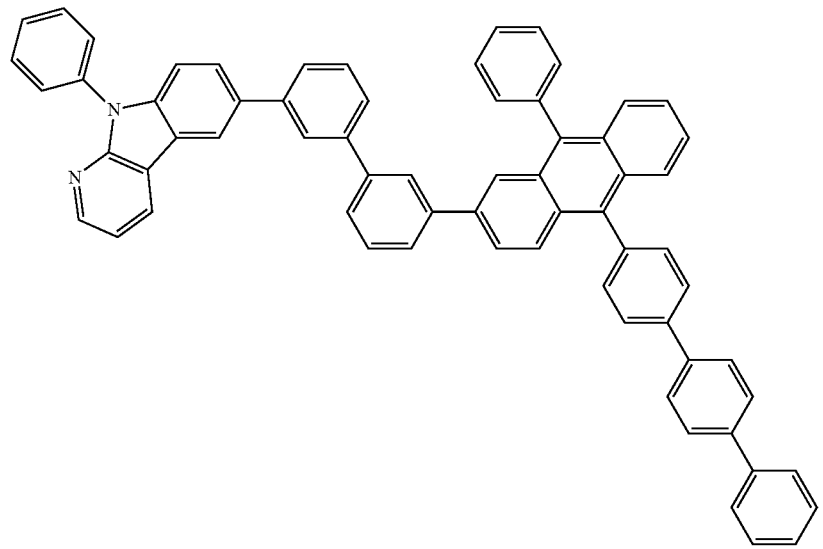
(Compound 100)

-continued
[Chem. 104]
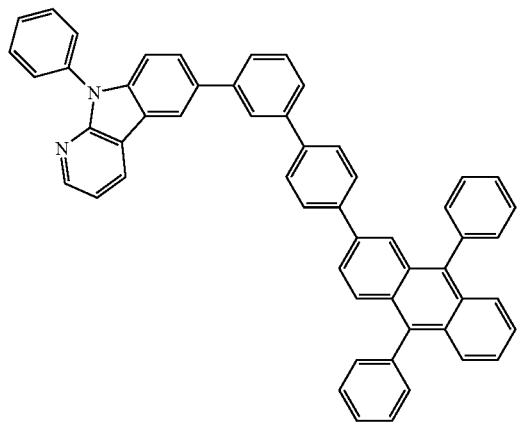
(Compound 101)
[Chem. 105]
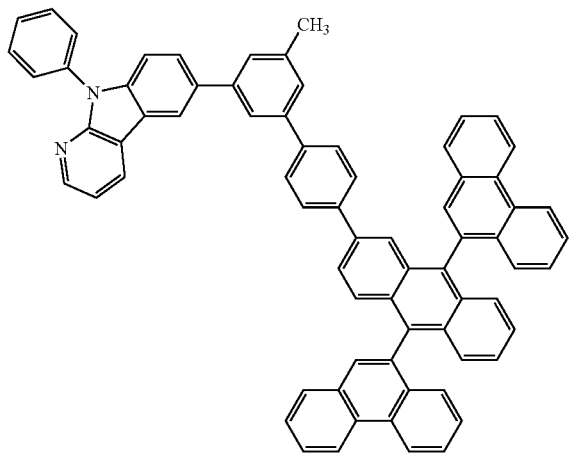
(Compound 102)
[Chem. 106]
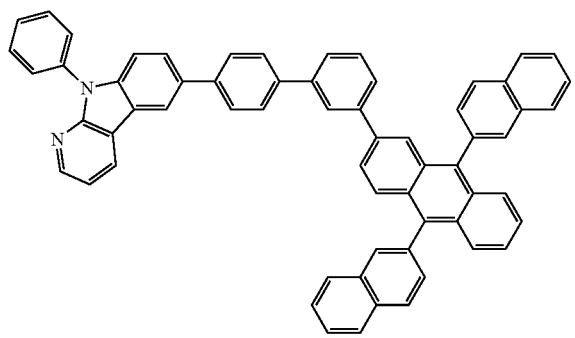
(Compound 103)
[Chem. 107]
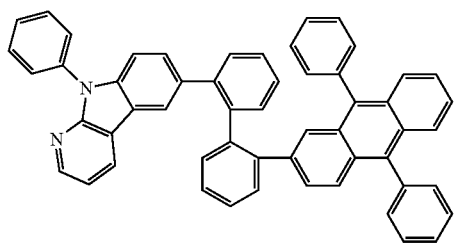
(Compound 104)
[Chem. 108]
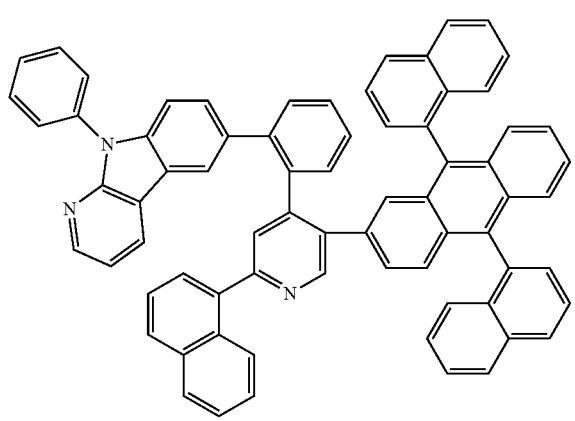
(Compound 105)

-continued
[Chem. 109]
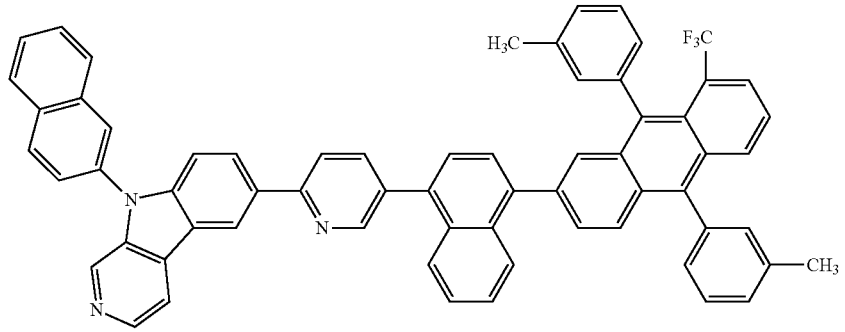
(Compound 106)
[Chem. 110]
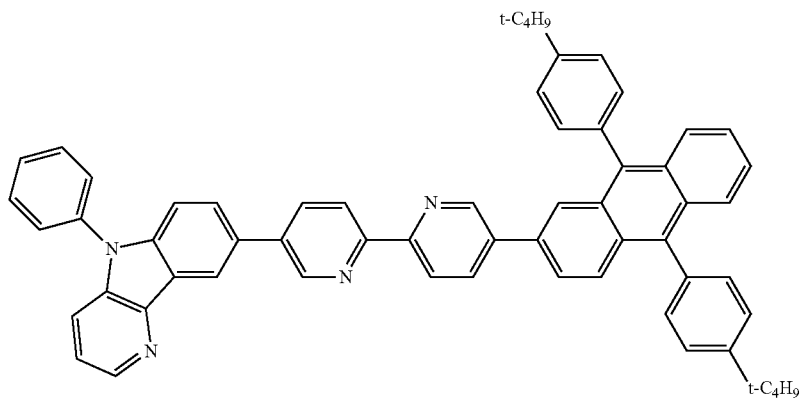
(Compound 107)
[Chem. 111]
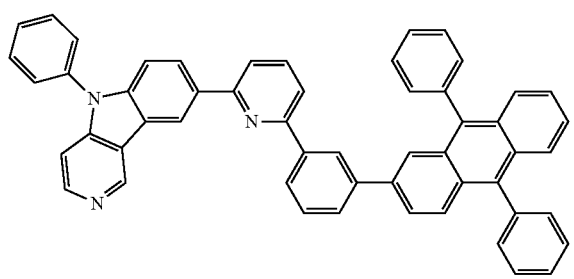
(Compound 108)
[Chem. 112]
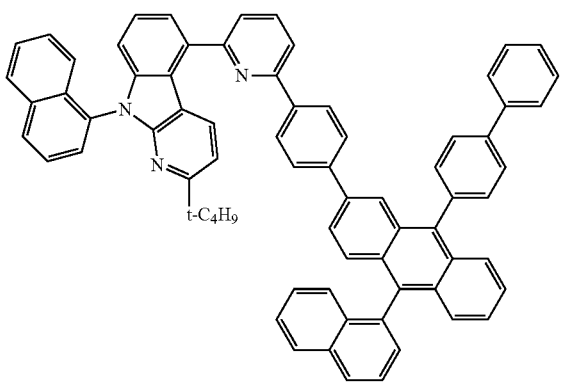
(Compound 109)

[Chem. 113]
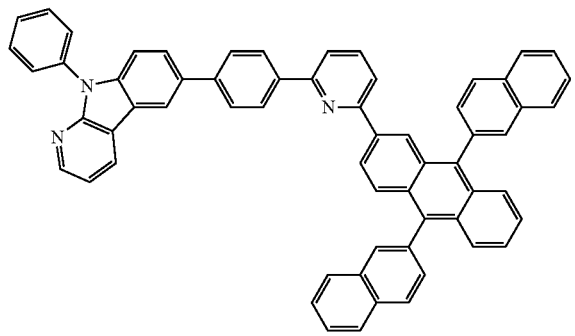
(Compound 110)
[Chem. 114]
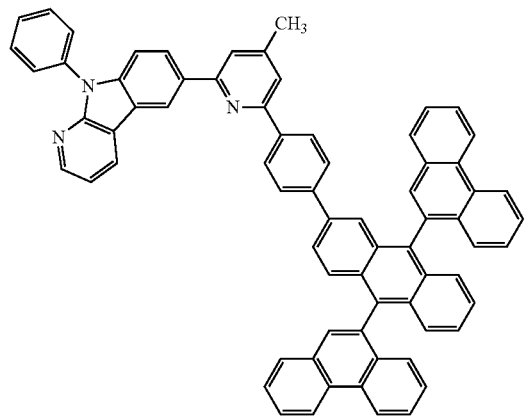
(Compound 111)
[Chem. 115]
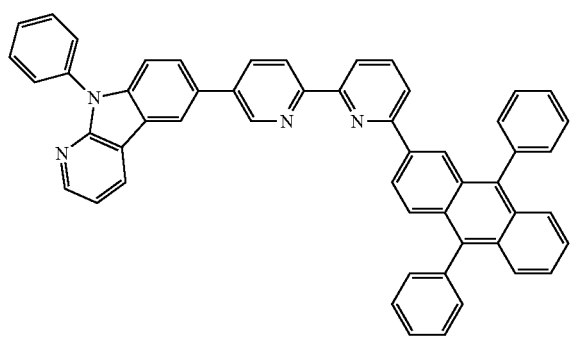
(Compound 112)
[Chem. 116]
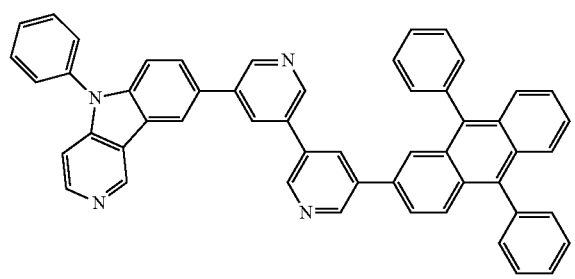
(Compound 113)
[Chem. 117]
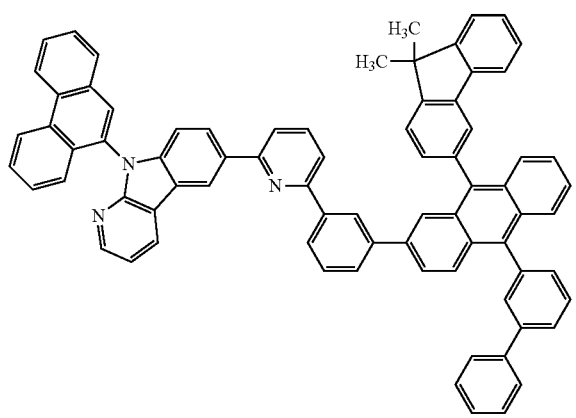
(Compound 114)
[Chem. 118]
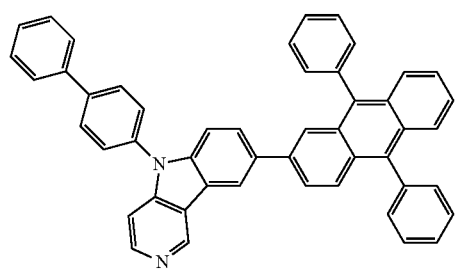
(Compound 115)

[Chem. 119]
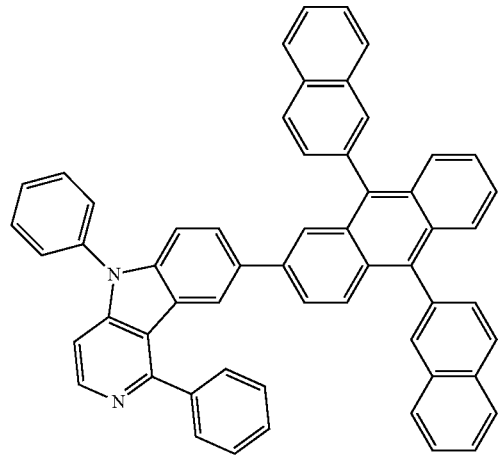
(Compound 116)
[Chem. 120]
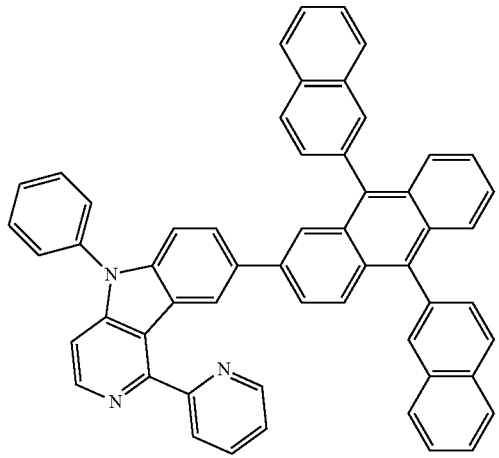
(Compound 117)
[Chem. 121]
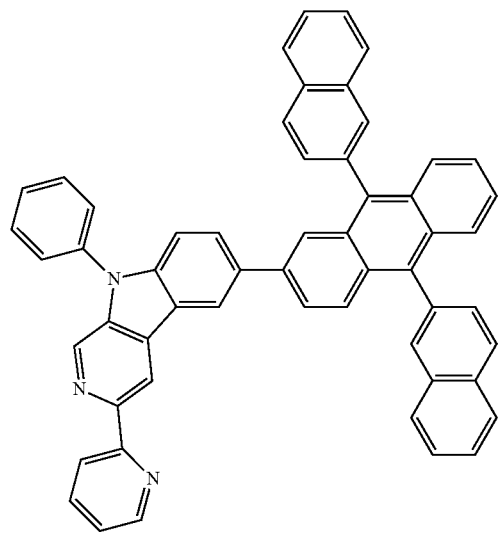
(Compound 118)
[Chem. 122]
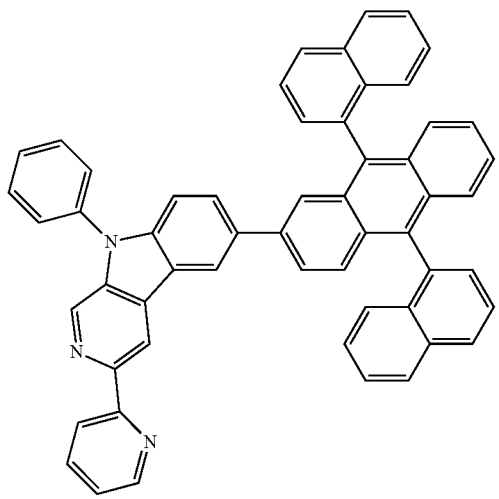
(Compound 119)

[Chem. 123]
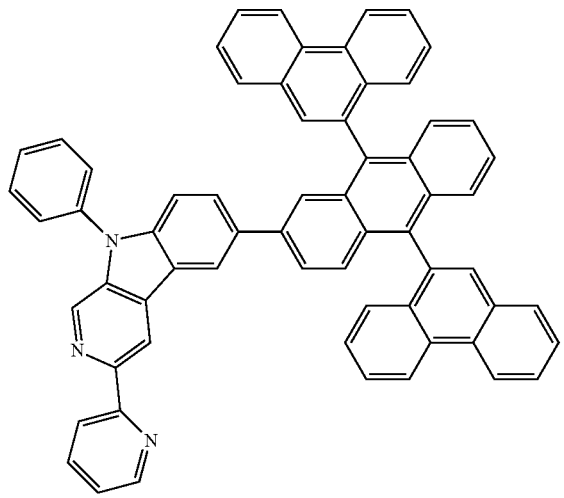
(Compound 120)
[Chem. 124]
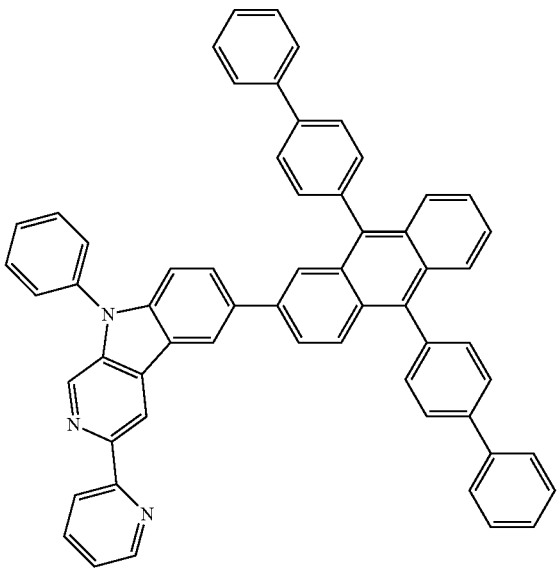
(Compound 121)
[Chem. 125]
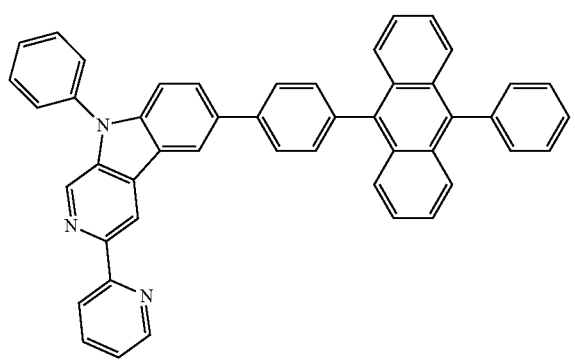
(Compound 122)
[Chem. 126]
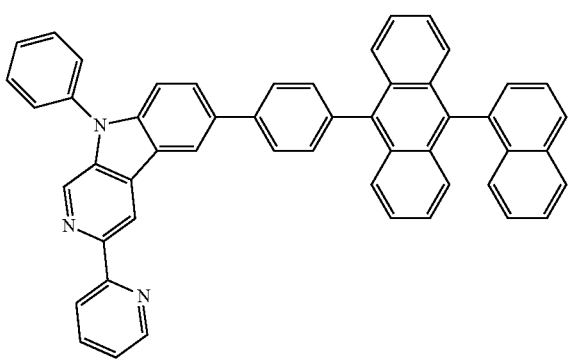
(Compound 123)
[Chem. 127]
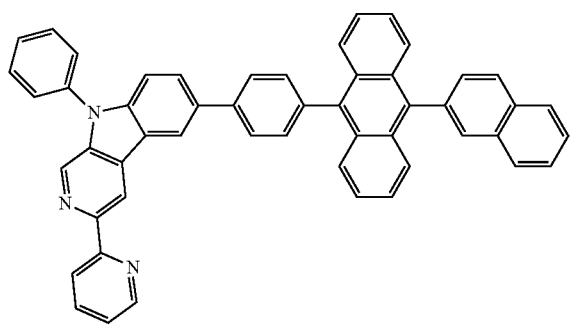
(Compound 124)
[Chem. 128]
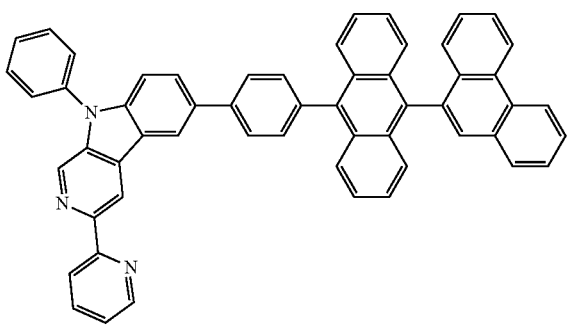
(Compound 125)

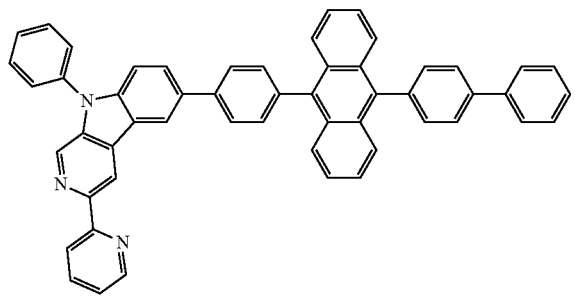

(Compound 126)

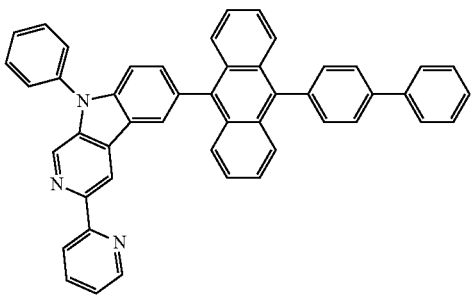

(Compound 127)

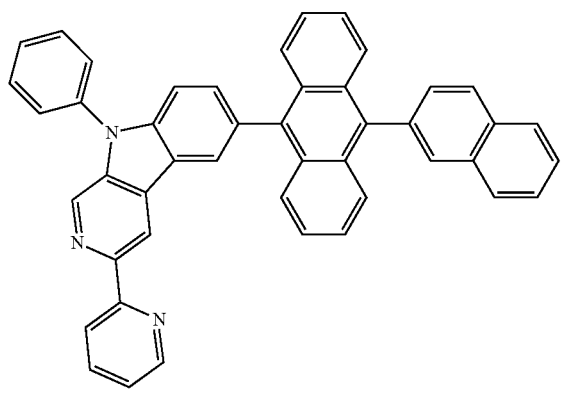

(Compound 128)

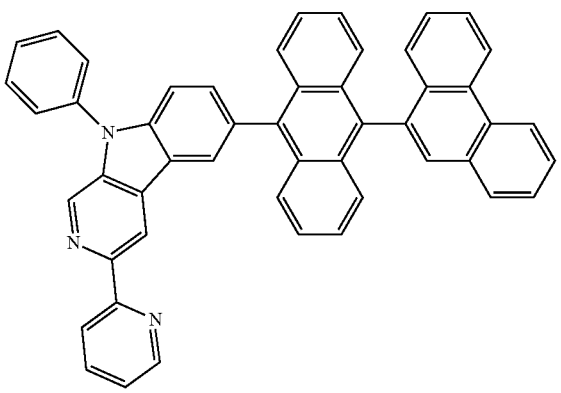

(Compound 129)

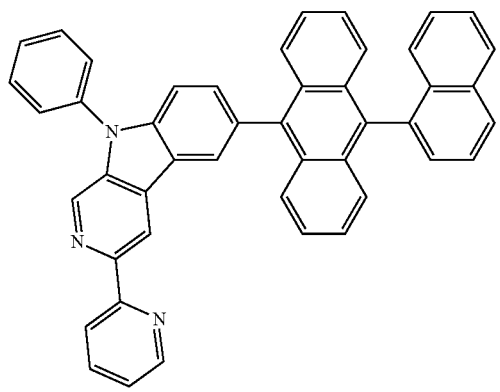

(Compound 130)

Purification of these compounds was performed by purification by column chromatography, adsorption purification with silica gel, active carbon, activated clay, or the like, a recrystallization or crystallization method with a solvent, or the like. Identification of the compounds was performed by NMR analysis. As physical properties, measurements of melting point, glass transition point (Tg) and work function were carried out. The melting point serves as an indicator of vapor deposition properties, the glass transition point (Tg) serves as an indicator of stability in thin-film state, and the work function serves as an indicator of hole-blocking ability.

The melting point and the glass transition point were measured using a powder material by means of a highly sensitive differential scanning calorimeter DSC 3100S manufactured by Bruker AXS. The melting point is preferably about 250° C. or higher, and the glass transition point is preferably about 100° C. or higher.

Further, the work function was measured by preparing a thin film of 100 nm in thickness on an ITO substrate and by using an atmospheric photoelectron spectroscopy AC-3 manufactured by Riken Keiki Co., Ltd.

In addition, regarding the stability under high temperature condition, a powder was sealed in a tube under vacuum condition and its samples before and after allowed to stand for one week in a thermostatic oven set to a predetermined temperature were subjected to the purity measurement using an analyzer such as high performance liquid chromatography, and changes in purity of the samples before and after that were evaluated. The stability under high temperature condition serves as an indicator of durability at the time of preparing or operating an organic EL device.

As the structure of the organic EL device of the present invention, there may be mentioned those which consist of an anode, a hole-transport layer, a light-emitting layer, a hole-blocking layer, an electron-transport layer and a cathode arranged on a substrate in that order, those which have a hole-injection layer between the anode and hole-transport layer, those which have an electron-injection layer between the electron-transport layer and cathode, and those which an electron-blocking layer between the light-emitting layer and hole-transport layer. It is possible to omit some of the organic layers in these multilayered structures, and for example, it is possible to make a structure in which the anode, hole-transport layer, light-emitting layer, electron-transport layer, and cathode are arranged on the substrate in that order.

Regarding the light-emitting layer, hole-transport layer and electron-transport layer, each of them may have a structure in which two or more layers are laminated.

As the anode of the organic EL device of the present invention, an electrode material having large work function such as ITO and gold can be used. As the hole-injection layer of the organic EL device of the present invention, there can be used a star burst type triphenylamine derivative; a triphenylamine trimer and tetramer such as an arylamine compound having, in the molecule, a structure in which three or more of triphenylamine structures are connected by a single bond or a divalent group which contains no hetero atom; an acceptor type heterocyclic compound such as hexacyanoazatriphenylene; and a coating type polymer material, in addition to a porphyrin compound typified by copper-phthalocyanine. Thin film forming with these materials can be carried out by a conventionally known method such as a spin coat method or an ink jet method, in addition to a vapor deposition method.

As the hole-transport layer of the organic EL device of the present invention, there may be used a benzidine derivative such as N,N'-diphenyl-N,N'-di(m-tolyl)-benzidine (referred to as TPD hereinafter), N,N'-diphenyl-N,N'-di(α-naphthyl)-benzidine (referred to as NPD hereinafter), and N,N,N',N'-tetrabiphenylbenzidine, 1,1-bis[(di-4-tolylamino)phenyl]cyclohexane (referred to as TAPC hereinafter), various triphenylamine trimers and tetramers, and the like. Each of these may be subjected to film-forming alone but may be used as a single layer prepared by mixing the material together with other materials and subjected to film-forming. There may be also employed a lamination structure of layers each prepared by subjecting one material to film-forming alone, of layers each prepared by subjecting one material to mixing and film-forming, or of a layer prepared by subjecting one material to film-forming alone and a layer prepared by subjecting one material to mixing and film-forming. In addition, as a hole-injection/transport layer, a coating type polymer material such as poly (3,4-ethylenedioxythiophene) (referred to as PEDOT hereinafter)/poly (styrene sulfonate) (referred to as PSS hereinafter) can be used. Thin film forming with these materials can be carried out by a conventionally known method such as a spin coat method or an ink jet method, in addition to a vapor deposition method.

Also, in the hole-injection layer or hole-transport layer, those in which trisbromophenylamine hexachloroantimony or the like is P-doped to a material generally used in the layer, a polymer compound having a TPD structure as its partial structure and the like can be further used.

As the electron-blocking layer of the organic EL device of the present invention, there can be used a compound having electron-blocking action, for example, a carbazole derivative such as 4,4',4''-tri(N-carbazolyl)triphenylamine (referred to as TCTA hereinafter), 9,9-bis[4-(carbazol-9-yl)phenyl]fluorene, 1,3-bis(carbazol-9-yl)benzene (referred to as mCP hereinafter), and 2,2-bis(4-carbazol-9-yl phenyl)adamantane (referred to as Ad-Cz hereinafter), and a compound having triphenylsilyl group and triarylamine structure typified by 9-[4-(carbazol-9-yl)phenyl]-9-[4-(triphenylsilyl)phenyl]-9H-fluorene. Each of these may be subjected to film-forming alone but may be used as a single layer prepared by mixing the material together with other materials and subjected to film-forming. There may be also employed a lamination structure of layers each prepared by subjecting one material to film-forming alone, of layers each prepared by subjecting one material to mixing and film-forming, or of a layer prepared by subjecting one material to film-forming alone and a layer prepared by subjecting one material to mixing and film-forming. Thin film forming with these materials can be carried out by a conventionally known method such as a spin coat method or an ink jet method, in addition to a vapor deposition method.

As the light-emitting layer of the organic EL device of the present invention, in addition to the compound having a substituted anthracene ring structure and a pyridoindole ring structure of the present invention, there can be used a metal complex of a quinolinol derivative such as $Alq_3$, various metal complexes, an anthracene derivative, a bisstyrylbenzene derivative, a pyrene derivative, an oxazole derivative, a polyparaphenylenevinylene derivative and the like. In addition, the light-emitting layer may be constituted from a host material and a dopant material, and as the host material, a thiazole derivative, a benzimidazole derivative, a polydialkylfluorene derivative and the like can be used in addition to the aforementioned light-emitting materials. Also, as the dopant material, there can be used quinacridone, coumalin, rubrene, perylene, and derivatives thereof, a benzopyran derivative, a Rhodamine derivative, an aminostyryl derivative and the like. Each of these may be subjected to film-forming alone but may be used as a single layer prepared by mixing the material together with other materials and subjected to film-forming. There may be also employed a lamination structure of layers each prepared by subjecting one material to film-forming alone, of layers each prepared by subjecting one material to mixing and film-forming, or of a layer prepared by subjecting one material to film-forming alone and a layer prepared by subjecting one material to mixing and film-forming.

In addition, it is also possible to use a phosphorescent light-emitting material as the light-emitting material. As the phosphorescent light-emitter, a phosphorescence light-emitter of a metal complex such as of iridium or platinum can be used. There may be used a green phosphorescence light-emitter such as $Ir(ppy)_3$, a blue phosphorescence light-emitter such as FIrpic, and FIr6, a red phosphorescence light-emitter such as $Btp_2Ir(acac)$, and the like. As the host material of this case, a carbazolyl derivative such as 4,4'-di(N-carbazolyl)biphenyl (referred to as CBP hereinafter), TCTA, and mCP, and the like can be used as a hole-injection/transport host material. As an electron-transport host material, p-bis(triphenylsilyl)benzene (referred to as UGH2 hereinafter), 2,2',2''-(1,3,5-phenylene)-tris(1-phenyl-1H-benzimidazole) (referred to as TPBI hereinafter) and the like can be used.

Doping of the phosphorescent light-emitting material to the host material is desirably carried out by co-deposition within the range of from 1% by weight to 30% by weight to the entire light-emitting layer, in order to avoid concentration quenching.

Thin film forming of these materials can be carried out by a conventionally known method such as a spin coat method or an ink jet method, in addition to the vapor deposition method.

As the hole-blocking layer of the organic EL device of the present invention, in addition to the compound having a substituted anthracene ring structure and a pyridoindole ring structure of the present invention, there can be used a compound having a hole-blocking action, for example, a phenanthroline derivative such as Bathocuproin (referred to as BCP hereinafter) and a quinolinol derivative metal complex such as BAlq, as well as various rare earth complexes, an oxazole derivative, a triazole derivative, a triazine derivative and the like. These materials may also serve as a material of the electron-transport layer. Each of these may be subjected to film-forming alone but may be used as a single layer prepared by mixing the material together with other materials and subjected to film-forming. There may be also employed a lamination structure of layers each prepared by subjecting one material to film-forming alone, of layers each prepared by subjecting one material to mixing and film-forming, or of a layer prepared by subjecting one material to film-forming alone and a layer prepared by subjecting one material to mixing and film-forming. Thin film forming with these materials can be carried out by a conventionally known method such as a spin coat method or an ink jet method, in addition to a vapor deposition method.

As the electron-transport layer of the organic EL device of the present invention, in addition to the compound having a substituted anthracene ring structure and a pyridoindole ring structure of the present invention, there can be used a quinolinol derivative metal complex such as $Alq_3$ and BAlq, as well as various metal complexes, a triazole derivative, a triazine derivative, an oxadiazole derivative, a thiadiazole derivative, a carbodiimide derivative, a quinoxaline derivative, a phenanthroline derivative, a silole derivative and the like. Each of these may be subjected to film-forming alone but may be used as a single layer prepared by mixing the material together with other materials and subjected to film-forming. There may be also employed a lamination structure of layers each prepared by subjecting one material to film-forming alone, of layers each prepared by subjecting one material to mixing and film-forming, or of a layer prepared by subjecting one material to film-forming alone and a layer prepared by subjecting one material to mixing and film-forming. Thin film forming with these materials can be carried out by a conventionally known method such as a spin coat method or an ink jet method, in addition to a vapor deposition method.

As the electron-injection layer of the organic EL device of the present invention, in addition to the compound having a substituted anthracene ring structure and a pyridoindole ring structure of the present invention, there can be used an alkali metal salt such as lithium fluoride or cesium fluoride, an alkaline earth metal salt such as magnesium fluoride, a metal oxide such as aluminum oxide, and the like, but these can be omitted in case of desirable selection of the electron-transport layer and cathode.

In addition, in the electron-injection layer or electron-transport layer, those in which a metal such as cesium was further N-doped to a material generally used in the layer can be used.

As the cathode of the organic EL device of the present invention, an electrode material having low work function, such as aluminum, and an alloy having further low work function, such as a magnesium silver alloy, a magnesium indium alloy, and an aluminum magnesium alloy, are used as the electrode materials.

The following describes embodiments of the present invention further illustratively based on examples, but the present invention is not limited to the following examples without departing its gist.

EXAMPLE 1

Synthesis of 8-[10-(naphthalen-2-yl)-anthracen-9-yl]-5-phenyl-5H-pyrido[4,3-b]indole (compound 10)

Into a nitrogen-purged reaction vessel, 43.0 ml of iodobenzene, 50.0 g of 5H-pyrido[4,3-b]indole, 1.9 g of copper powder, 82.2 g of potassium carbonate, and 2.1 ml of dimethyl sulfoxide were added, then, heated and stirred at 170° C. for 3 hours. After cooling to 100° C., 500 ml of toluene was added thereto followed by stirring at 100° C. for 1 hour. After removing the insoluble matter by filtration, the filtrate was concentrated under a reduced pressure to thereby obtain a crude product. The crude product was purifying by using a column chromatography (carrier: NH silica gel, eluent: toluene), to thereby obtain 69.9 g (yield 96%) of 5-phenyl-5H-pyrido[4,3-b]indole as a yellow liquid.

Into a nitrogen-purged reaction vessel, 27.2 g portion of the thus obtained 5-phenyl-5H-pyrido[4,3-b]indole and 150 ml of dimethyl formamide were added, then, heated while adding 23.8 g of N-bromosuccinimide with stirred, and stirred at 50° C. for 10 hours. After cooling to room temperature, 300 ml of chloroform and 300 ml of water were added thereto and then stirred, and thereafter, the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene/hexane), to thereby obtain 18.0 g (yield 50%) of 8-bromo-5-phenyl-5H-pyrido[4,3-b]indole as a yellow liquid.

Into a nitrogen-purged reaction vessel, 1.9 g portion of the thus obtained 8-bromo-5-phenyl-5H-pyrido[4,3-b]indole, 3.0 g of 9-(4,4,5,5-tetramethyl-[1,3,2]dioxaborolan-2-yl)-10-naphthalen-2-yl-anthracene, 0.2 g of tetrakis(triphenylphosphine)palladium, 14 ml of 2 M potassium carbonate aqueous solution, 36 ml of toluene, and 9 ml of ethanol were added and heated, and refluxed for 19 hours while stirring. After cooling to room temperature, 100 ml of toluene and 50 ml of water were added thereto, followed by stirring, and thereafter, the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene/hexane), to thereby obtain 1.7 g (yield 53%) of 8-[10-(naphthalen-2-yl)-anthracen-9-yl]-5-phenyl-5H-pyrido[4,3-b]indole (compound 10) as a pale yellow powder.

Structure of the thus obtained pale yellow powder was identified using NMR. Results of the $^1$H-NMR measurement are shown in FIG. 1.

The following 26 signals of hydrogen were detected by $^1$H-NMR (CDCl$_3$). δ (ppm)=9.38 (1H), 8.58 (1H), 8.36 (1H), 8.09 (1H), 8.02 (2H), 7.94 (1H), 7.77 (4H), 7.69 (5H), 7.56-7.65 (5H), 7.39 (1H), 7.33 (4H).

EXAMPLE 2

Synthesis of 8-(9,10-diphenylanthracen-2-yl)-5-phenyl-5H-pyrido[4,3-b]indole (compound 75)

Into a nitrogen-purged reaction vessel, 2.8 g portion of the aforementioned 8-bromo-5-phenyl-5H-pyrido[4,3-b]indole obtained in Example 1, 3.6 g of 9,10-diphenylanthracene-2-boronic acid, 0.1 g of tetrakis(triphenylphosphine) palladium, 22 ml of 2 M potassium carbonate aqueous solution, 60 ml of toluene, and 15 ml of ethanol were added and heated, and refluxed for 16 hours while stirring. After cooling to room temperature, 100 ml of toluene and 100 ml of saturated brine were added thereto, followed by stirring, and thereafter, the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene/hexane), to thereby obtain 3.0 g (yield 61%) of 8-(9,10-diphenylanthracen-2-yl)-5-phenyl-5H-pyrido[4,3-b]indole (compound 75) as a yellow powder.

Figure 2:
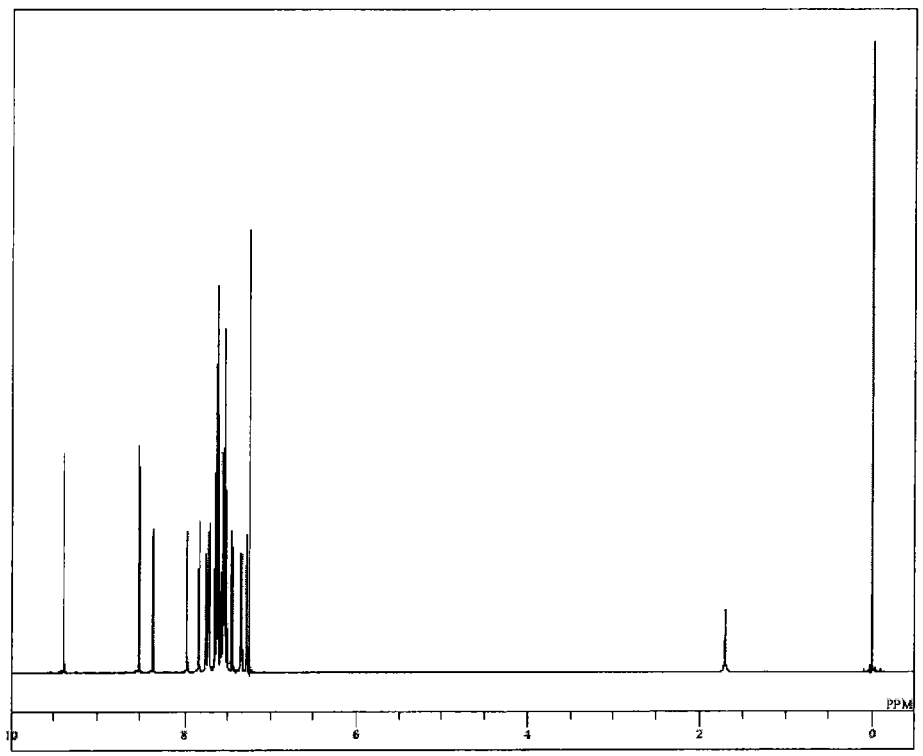
FIG. 2 is a 1H-NMR chart of the compound (Compound 75) of Invention Example 2.

Structure of the thus obtained yellow powder was identified using NMR. Results of the $^1$H-NMR measurement are shown in FIG. 2.

The following 28 signals of hydrogen were detected by $^1$H-NMR (CDCl$_3$). δ (ppm)=9.39 (1H), 8.52 (1H), 8.36 (1H), 7.98 (1H), 7.84 (1H), 7.74 (3H), 7.50-7.67 (16H), 7.45 (1H), 7.35 (2H), 7.29 (1H).

EXAMPLE 3

Synthesis of 8-[9,10-di(naphthalen-2-yl)-anthracen-2-yl]-5-phenyl-5H-pyrido[4,3-b]indole
(compound 78)

Into a nitrogen-purged reaction vessel, 2.0 g portion of the aforementioned 8-bromo-5-phenyl-5H-pyrido[4,3-b]indole obtained in Example 1, 3.5 g of 9,10-di(naphthalen-2-yl)anthracene-2-boronic acid, 0.4 g of tetrakis(triphenylphosphine) palladium, 10 ml of 2 M potassium carbonate aqueous solution, 20 ml of toluene, and 5 ml of ethanol were added and heated, and refluxed for 5.5 hours while stirring. After cooling to room temperature, 50 ml of toluene and 30 ml of water were added thereto, followed by stirring, and thereafter, the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene), to thereby obtain 2.2 g (yield 53%) of 8-[9,10-di(naphthalen-2-yl)-anthracen-2-yl]-5-phenyl-5H-pyrido[4,3-b]indole (compound 78) as a yellow powder.

Figure 3:
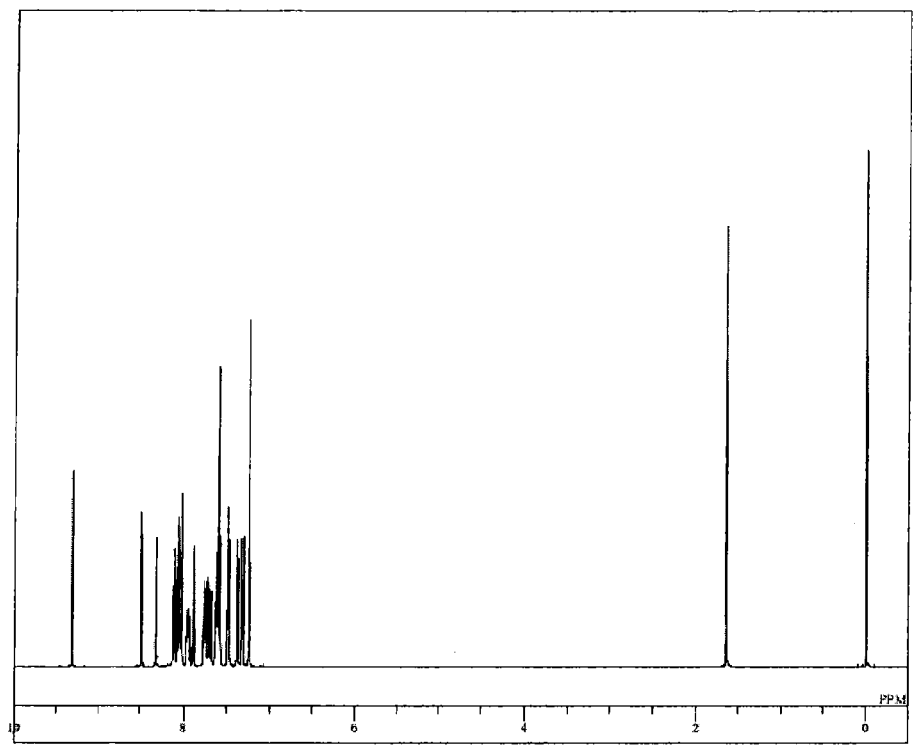
FIG. 3 is a $^1$H-NMR chart of the compound (Compound 78) of Invention Example 3.

Structure of the thus obtained yellow powder was identified using NMR. Results of the $^1$H-NMR measurement are shown in FIG. 3.

The following 32 signals of hydrogen were detected by $^1$H-NMR (CDCl$_3$). δ (ppm)=9.32 (1H), 8.48 (1H), 8.32 (1H), 8.11 (2H), 8.02-8.07 (5H), 7.95 (2H), 7.88 (1H), 7.68-7.78 (5H), 7.58-7.64 (7H), 7.49 (3H), 7.37 (1H), 7.33 (2H), 7.24 (1H).

EXAMPLE 4

Synthesis of 8-[4-[10-(naphthalen-2-yl)anthracen-9-yl]phenyl]-5-phenyl-5H-pyrido[4,3-b]indole
(compound 16)

Into a nitrogen-purged reaction vessel, 4.0 g of 8-(4-bromophenyl)-5-phenyl-5H-pyrido[4,3,b-]indole, 4.1 g of 10-(naphthalen-2-yl)anthracene-9-boronic acid, 0.3 g of tetrakis(triphenylphosphine) palladium, 15 ml of 2 M potassium carbonate aqueous solution, 32 ml of toluene, and 8 ml of ethanol were added and heated, and refluxed for 18 hours while stirring. After cooling to room temperature, the precipitate was collected by filtration. The precipitate was dissolved in 1,2-dichlorobenzene while heating, the insoluble matter was removed by filtration, and then the filtrate was concentrated under a reduced pressure, to thereby obtain a crude product. The crude product was purified by recrystallization using 1,2-dichlorobenzene, to thereby obtain 2.5 g (yield 40%) of 8-[4-(10-naphthalen-2-yl-anthracen-9-yl)-phenyl]-5-phenyl-5H-pyrido[4,3-b]indole (compound 16) as a yellow powder.

Figure 4:
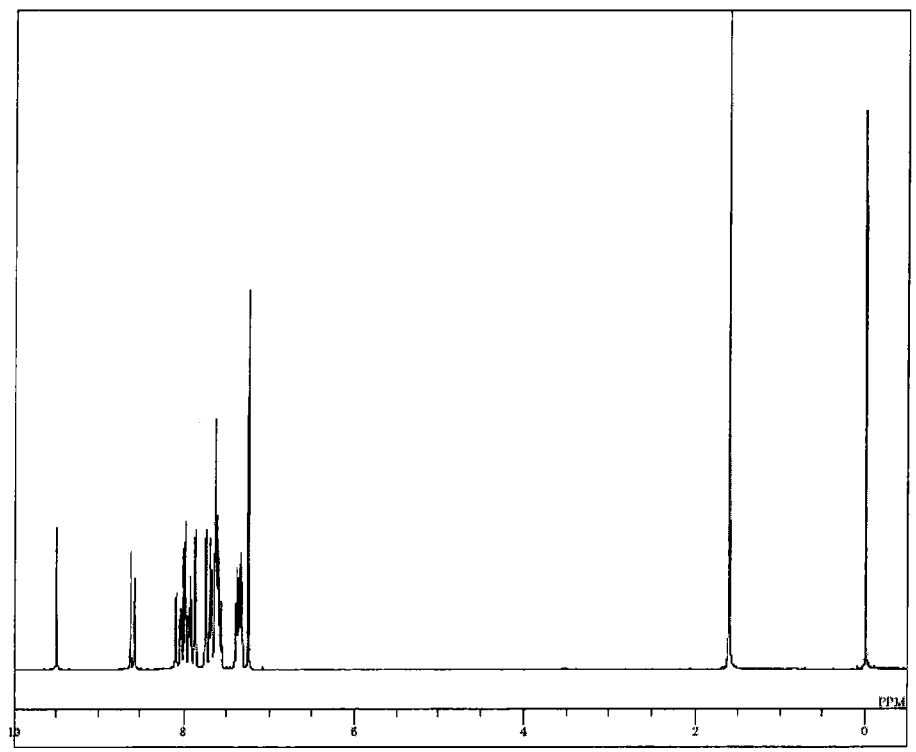
FIG. 4 is a 1H-NMR chart of the compound (Compound 16) of Invention Example 4.

Structure of the thus obtained yellow powder was identified using NMR. Results of the $^1$H-NMR measurement are shown in FIG. 4.

The following 30 signals of hydrogen were detected by $^1$H-NMR (CDCl$_3$). δ (ppm)=9.50 (1H), 8.62 (1H), 8.57 (1H), 8.09 (1H), 8.04 (1H), 7.99 (3H), 7.92 (2H), 7.87 (2H), 7.75 (2H), 7.66-7.72 (2H), 7.55-7.66 (9H), 7.30-7.40 (5H).

EXAMPLE 5

Synthesis of 5-(biphenyl-4-yl)-8-(9,10-diphenylanthracen-2-yl)-5H-pyrido[4,3-b]indole
(compound 115)

Into a nitrogen-purged reaction vessel, 3.5 g of 5-(biphenyl-4-yl)-8-bromo-5H-pyrido[4,3-b]indole, 3.6 g of 9,10-diphenylanthracene-2-boronic acid, 0.1 g of tetrakis(triphenylphosphine) palladium, 22 ml of 2 M potassium carbonate aqueous solution, 35 ml of toluene, and 9 ml of ethanol were added and heated, and refluxed for 4 hours while stirring. After cooling to room temperature, 100 ml of toluene and 100 ml of saturated brine were added thereto followed by stirring, and thereafter, the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene), to thereby obtain 3.0 g (yield 52%) of 5-(biphenyl-4-yl)-8-(9,10-diphenylanthracen-2-yl)-5H-pyrido[4,3-b]indole (compound 115) as a yellow powder.

Figure 5:
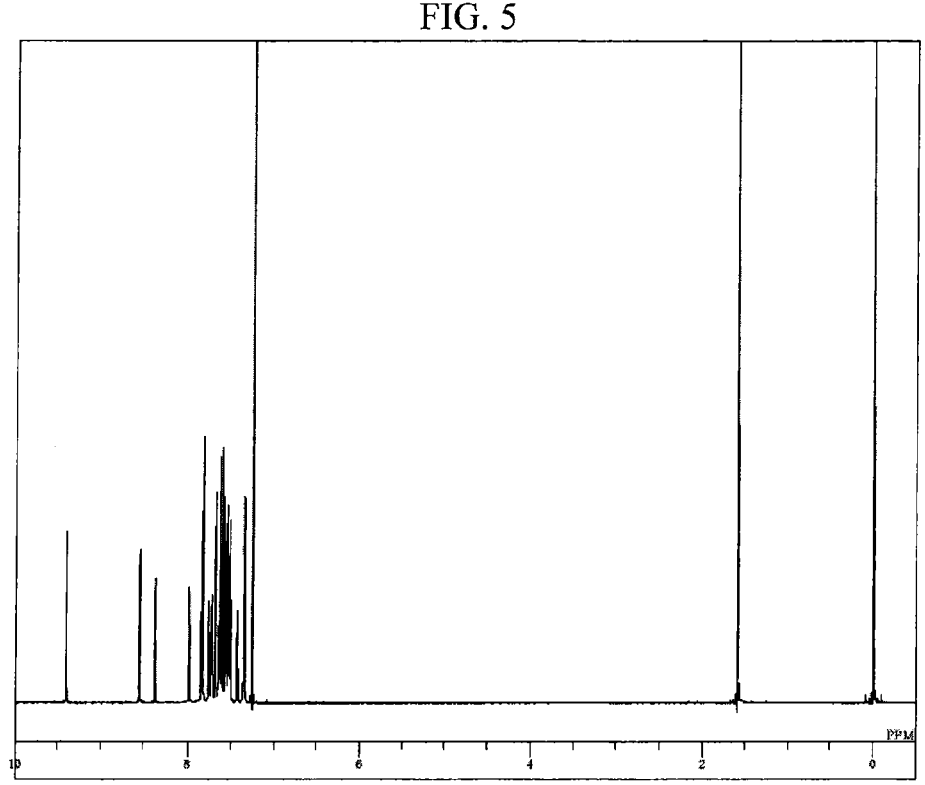
FIG. 5 is a $^1$H-NMR chart of the compound (Compound 115) of Invention Example 5.

Structure of the thus obtained yellow powder was identified using NMR. Results of the $^1$H-NMR measurement are shown in FIG. 5.

The following 32 signals of hydrogen were detected by $^1$H-NMR (CDCl$_3$). δ (ppm)=9.40 (1H), 8.55 (1H), 8.37 (1H), 7.99 (1H), 7.84 (3H), 7.74 (3H), 7.69 (3H), 7.50-7.66 (15H), 7.43 (1H), 7.35 (3H).

EXAMPLE 6

Synthesis of 8-[9,10-di(naphthalen-2-yl)-anthracen-2-yl]-1,5-diphenyl-5H-pyrido[4,3-b]indole
(compound 116)

Into a nitrogen-purged reaction vessel, 4.9 g portion of the aforementioned 8-[9,10-di(naphthalen-2-yl)-anthracen-2-yl]-5-phenyl-5H-pyrido[4,3-b]indole (compound 78) obtained in Example 3 and 100 ml of tetrahydrofuran were added and cooled to −18° C., and then 7.6 ml of phenyllithium solution of 1.9 mol/l was added dropwise thereto, followed by stirring for 3 hours. After adding 30 ml of ammonium chloride aqueous solution thereto while cooling to 0° C., 50 ml of toluene was added thereto, followed by stirring, and the organic layer was separated. The organic layer was dehydrated using anhydrous magnesium sulfate and then concentrated under a reduced pressure, to thereby obtain a crude product. The crude product was purified by using a column chromatography (carrier: NH silica gel, eluent: toluene), to thereby obtain 1.2 g (yield 22%) of 8-[9,10-di(naphthalen-2-yl)-anthracen-2-yl]-1,5-diphenyl-5H-pyrido[4,3-b]indole (compound 116) as a yellow powder.

Figure 6:
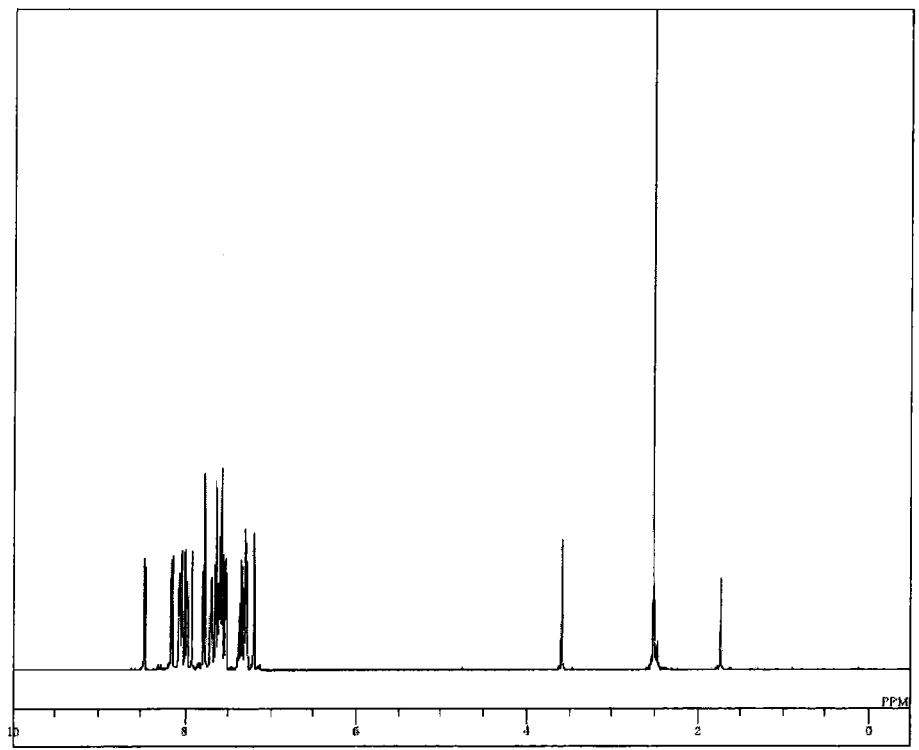
FIG. 6 is a 1H-NMR chart of the compound (Compound 116) of Invention Example 6.

Structure of the thus obtained yellow powder was identified using NMR. Results of the $^1$H-NMR measurement are shown in FIG. 6.

The following 36 signals of hydrogen were detected by $^1$H-NMR (THF-d$_8$). δ (ppm)=8.47 (1H), 8.15 (2H), 8.05 (4H), 8.00 (1H), 7.98 (2H), 7.92 (1H), 7.78 (3H), 7.70 (2H), 7.52-7.66 (13H), 7.28-7.39 (6H), 7.20 (1H).

EXAMPLE 7

On the compounds of Examples 1 to 6 of the present invention, melting point and glass transition point were determined by means of a highly sensitive differential scanning calorimeter (DSC 31005, manufactured by Bruker AXS).

|  | Melting point | Glass transition point |
|---|---|---|
| Compound of Inventive Example 1 | 304° C. | 163° C. |
| Compound of Inventive Example 2 | 284° C. | 141° C. |
| Compound of Inventive Example 3 | 282° C. | 172° C. |
| Compound of Inventive Example 4 | 350° C. | 164° C. |
| Compound of Inventive Example 5 | 274° C. | 158° C. |
| Compound of Inventive Example 6 | 333° C. | 193° C. |

The compounds of the present invention have a glass transition point of 100° C. or more. This shows that the compounds of the present invention are stable in thin-film state.

EXAMPLE 8

Using the compounds of Examples 1 to 3, 5 and 6 of the present invention, a deposited film having a film thickness of 100 nm was prepared on an ITO substrate and work function was measured using a photo-electron spectroscopy in air (Model AC-3, manufactured by Riken Keiki Co., Ltd.).

|  | Work function |
|---|---|
| Compound of Inventive Example 1 | 5.80 eV |
| Compound of Inventive Example 2 | 5.78 eV |
| Compound of Inventive Example 3 | 5.75 eV |
| Compound of Inventive Example 5 | 5.79 eV |
| Compound of Inventive Example 6 | 5.77 eV |

Thus, it can be seen that the compounds of the present invention have a large hole-blocking ability, because these have a work function value of larger than 5.4 eV which is possessed by the general hole-transport materials such as NPD or TPD and also have a work function value of larger than 5.6 eV which is possessed by Alq$_3$.

EXAMPLE 9

Using the compounds of Examples 1 to 3 of the present invention, a heat resistance test was carried out in order to verify their stability under high temperature condition. The heat resistance test was carried out in the following manner. That is, 10 mg of each of the compounds of Examples 1 to 3 of the present invention was put into a glass test tube and, after evacuation using a diaphragm type pump, the end of the glass tube was sealed. The thus sealed glass tube was put into a thermostatic oven set to a predetermined temperature of from 300° C. to 330° C. and allowed to stand for 1 week, and then the sealing was opened to be used as the sample after test. Samples before and after the heat resistance test were subjected to HPLC measurement (measuring conditions: column; Inertcil ODS-SP manufactured by GL Sciences Inc., inner diameter of 4.6 mm, length of 250 mm, eluent; methanol/0.05% (v/v) trifluoroacetic acid aqueous solution=8/2 (v/v), flow rate; 1.0 ml/min, column temperature; 40° C., measuring wavelength; 254 nm), and HPLC purity (peak area percentage, %) of the compounds of the present invention in respective samples was calculated from the thus obtained HPLC charts using a data processor. Those in which the purity reduction of sample before and after the heat resistance test was less than 5% based on the peak area percentage was regarded as "A (heat resistant)", and those having 5% or more as "B (no heat resistance)". Results of the heat resistance test of respective samples are as follows.

|  | Result of heat resistance test | [Temperature tested] |
|---|---|---|
| Compound of Inventive Example 1 | A | [330° C.] |
| Compound of Inventive Example 2 | A | [330° C.] |
| Compound of Inventive Example 3 | A | [330° C.] |
| BCP (comparative compound) | B | [300° C.] |

Thus, the compounds of the present invention are stably present under high temperature condition, because its purity reduction is less than 5% by peak area percentage. On the other hand, purity reduction of the comparative compound BCP (compound 131 of the following structure formula) is 5% or more by peak area percentage, revealing that the compounds of the present invention are excellent in heat resistance.

[Chem. 134]

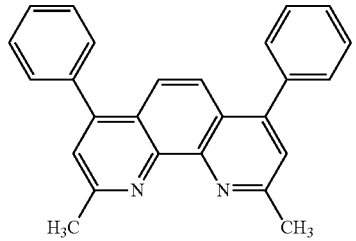

(Compound 131)

EXAMPLE 10

Figure 7:
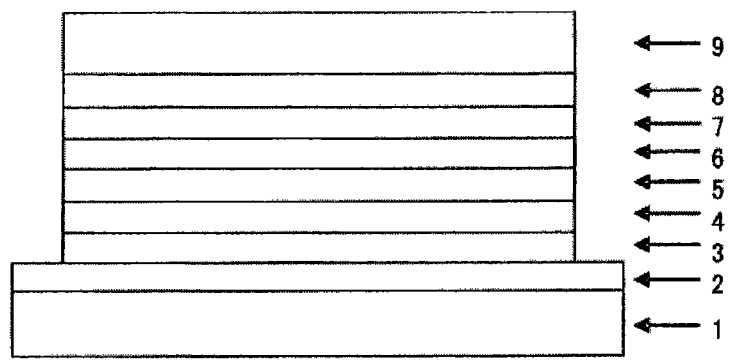
FIG. 7 This is a drawing showing the constitution of the EL devices of Examples 10 to 12, and Comparative Example 1.

As shown in FIG. 7, an organic EL device was prepared by forming an ITO electrode as the transparent anode 2 on the glass substrate 1 in advance and then depositing thereon the hole-injection layer 3, hole-transport layer 4, light-emitting layer 5, hole-blocking layer 6, electron transport layer 7, electron injection layer 8 and cathode (aluminum electrode) 9 in that order.

Specifically, the glass substrate 1 on which ITO of 150 nm in film thickness was formed was washed with an organic solvent and then its surface was washed by an oxygen plasma treatment. Thereafter, this glass substrate equipped with ITO electrode was attached to the inside of a vacuum deposition machine and decompressed to 0.001 Pa or less. Subsequently, as the hole-injection layer 3, compound 132 of the following structural formula was formed at a deposition rate of 6 nm/min to a film thickness of 20 nm such that the transparent anode 2 was covered therewith. On this hole-injection layer 3, compound 133 of the following structural formula was formed at a deposition rate of 6 nm/min to a film thickness of 40 nm as the hole-transport layer 4. On this hole-transport layer, compound 134 of the following structural formula and compound 135 of the following structural formula were formed to a film thickness of 30 nm as the light-emitting layer 5, by carrying out their binary deposition at a deposition rate of compound 134:compound 135=5:95 as the deposition rate ratio. On this light-emitting layer 5, the compound of Example 1 of the present invention (compound 10) was formed at a deposition rate of 6 nm/min to a film thickness of 30 nm as the hole-blocking layer 6-cum-the electron transport layer 7. On this hole-blocking layer-cum-electron transport layer 6 and 7, lithium fluoride was formed at a deposition rate of 0.6 nm/min to a film thickness of 0.5 nm as the electron injection layer 8. Finally, aluminum was deposited to a film thickness of 150 nm to form the cathode 9. On the thus prepared organic EL device, characteristics measurement was carried out in the air at ordinary temperature.

Direct current voltage was applied to the organic EL device prepared using the compound of Example 1 of the present invention (compound 10), and light emission characteristics in that case were measured, with the results shown en bloc in Table 1.

[Chem. 135]

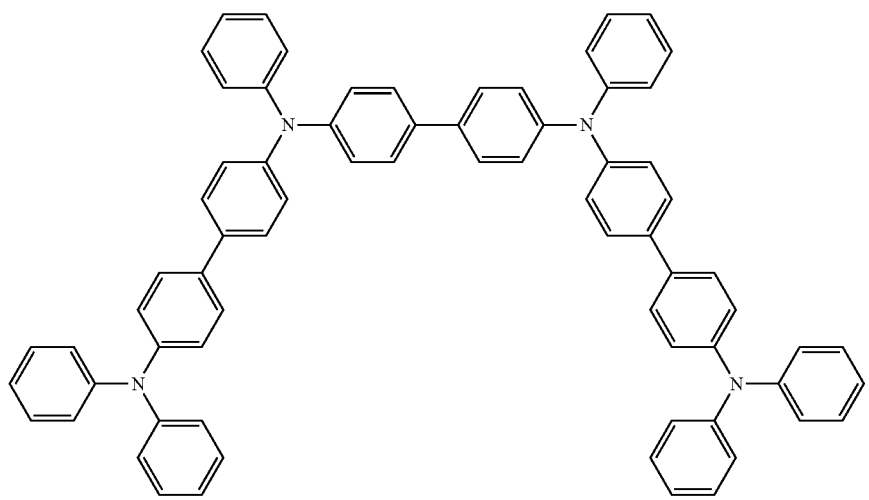

(Compound 132)

[Chem. 136]

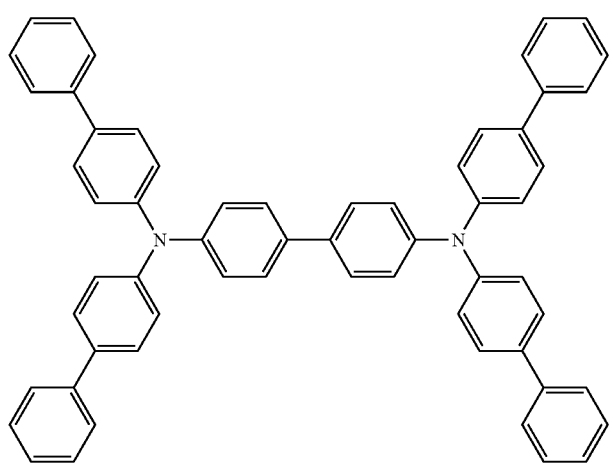

(Compound 133)

[Chem. 137]

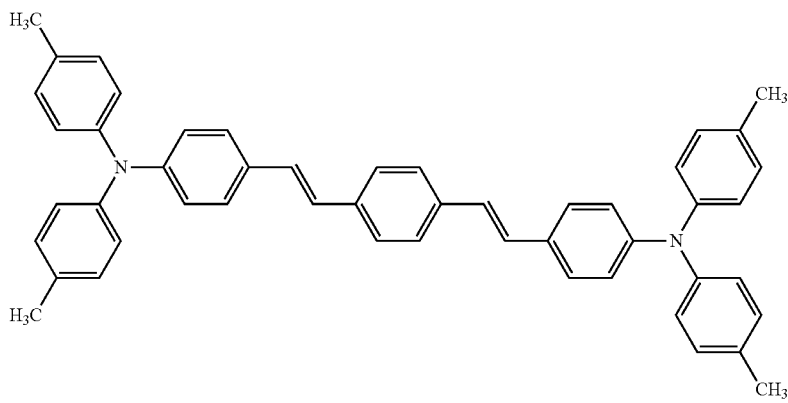

(Compound 134)

[Chem. 138]

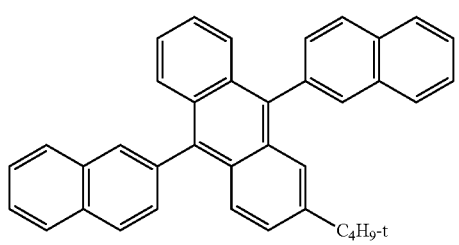

(Compound 135)

EXAMPLE 11

An organic EL device was prepared in the same manner as in Example 10, except that the compound of Example 2 of the present invention (compound 75) was used in place of the compound of Example 1 of the present invention (compound 10) as a material of the hole-blocking layer 6-cum-electron transport layer 7, and formed to a film thickness of 30 nm. On the thus prepared organic EL device, characteristics measurement was carried out in the air at ordinary temperature. Direct current voltage was applied to the thus prepared organic EL device, and light emission characteristics in that case were measured, with the results shown en bloc in Table 1.

EXAMPLE 12

An organic EL device was prepared in the same manner as in Example 10, except that the compound of Example 3 of the present invention (compound 78) was used in place of the compound of Example 1 of the present invention (compound 10) as a material of the hole-blocking layer 6-cum-electron transport layer 7, and formed to a film thickness of 30 nm. On the thus prepared organic EL device, characteristics measurement was carried out in the air at ordinary temperature. Direct current voltage was applied to the thus prepared organic EL device, and light emission characteristics in that case were measured, with the results shown en bloc in Table 1.

Comparative Example 1

For the sake of comparison, an organic EL device was prepared in the same manner as in Example 10, except that compound 136 of the following structural formula (e.g., see Patent Document 4) was used in place of the compound of Example 1 of the present invention (compound 10) as a material of the hole-blocking layer 6-cum-electron transport layer 7, and formed to a film thickness of 30 nm. On the thus prepared organic EL device, characteristics measurement was carried out in the air at ordinary temperature. Direct current voltage was applied to the thus prepared organic EL device, and light emission characteristics in that case were measured, with the results shown en bloc in Table 1.

[Chem. 139]

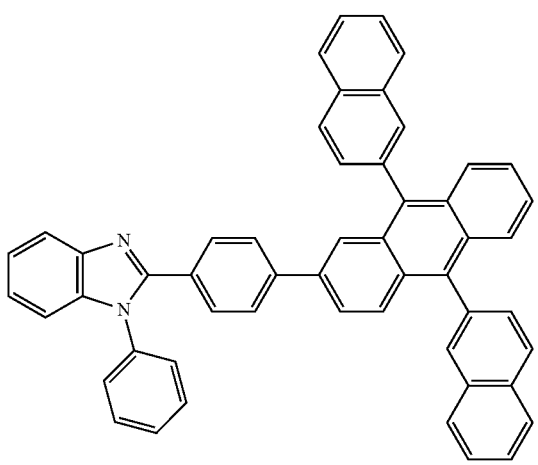

(Compound 136)

TABLE 1

| | Compound | Driving voltage (V) (@10 mA/cm$^2$) | Luminance [cd/m$^2$] (@10 mA/cm$^2$) | Luminous efficacy [cd/A] (@10 mA/cm$^2$) | Power efficacy [lm/W] (@10 mA/cm$^2$) |
|---|---|---|---|---|---|
| Ex. 10 | Comp. 10 | 5.24 | 871 | 8.71 | 5.23 |
| Ex. 11 | Comp. 75 | 3.94 | 932 | 9.32 | 7.43 |
| Ex. 12 | Comp. 78 | 4.15 | 972 | 9.72 | 7.36 |
| Comp. Ex. 1 | Comp. 136 | 5.95 | 792 | 7.92 | 4.19 |

As shown in Table 1, the driving voltage at the time of a current density of 10 mA/cm$^2$ was 5.95 V in the case of Comparative Example 1 in which the compound 136 of the aforementioned structural formula was used, but showed a lowered voltage of from 3.94 V to 5.24 V in all cases of Examples 10 to 12, and further, each of the luminance, luminous efficacy and power efficacy at the time of a current density of 10 mA/cm$^2$ was also improved.

Light emission initiation voltage was measured using the same organic EL devices as mentioned in the above, with the results shown below.

| Organic EL device | Compound | Light emission initiation voltage [V] |
|---|---|---|
| Example 10 | Compound 10 | 3.0 |
| Example 11 | Compound 75 | 2.8 |
| Example 12 | Compound 78 | 2.8 |
| Comp. Ex. 1 | Compound 136 | 3.1 |

As a result, it can be seen that, in comparison with the comparative Example 1 in which the compound 136 of the aforementioned structural formula was used, the light emission initiation voltage was lowered in Examples 10 to 12.

Thus, it was found that the organic EL devices of the present invention are excellent in the luminous efficacy and power efficacy and can attain significant lowering of the practical driving voltage, in comparison with the device prepared by using the compound 136 of the aforementioned structural formula which is used as a general electron-transport material.

While the present invention has been described in detail and with reference to specific embodiments thereof, it will be apparent to one skilled in the art that various changes and modifications can be made therein without departing from the spirit and scope of the present invention.

This application is based on Japanese Patent Application No. 2009-258613 filed on Nov. 12, 2009, the entire contents of which are incorporated herein by reference.

INDUSTRIAL APPLICABILITY

The compound having a substituted anthracene ring structure and a pyridoindole ring structure of the present invention is excellent as a compound for an organic EL device, because it has good electron injection performances, is excellent in hole-blocking ability, is excellent in heat resistance, and is stable in thin-film state. By preparing an organic EL device using the compound, high efficiency can be obtained and also the driving voltage can be lowered so that durability can be improved. For example, its development for applications such as domestic electric appliances and illumination became possible.

DESCRIPTION OF REFERENCE NUMERALS AND SIGNS

1 Glass substrate
2 Transparent anode
3 Hole-injection layer
4 Hole-transport layer
5 Light-emitting layer
6 Hole-blocking layer
7 Electron-transport layer
8 Electron-injection layer
9 Cathode

| | DESCRIPTION OF REFERENCE NUMERALS AND SIGNS |
|---|---|
| 1 | Glass substrate |
| 2 | Transparent anode |
| 3 | Hole-injection layer |
| 4 | Hole-transport layer |
| 5 | Light-emitting layer |
| 6 | Hole-blocking layer |
| 7 | Electron-transport layer |
| 8 | Electron-injection layer |
| 9 | Cathode |

The invention claimed is:

1. A compound having a substituted anthracene ring structure and a pyridoindole ring structure, which is represented by the following general formula (1) or the following general formula (2):

[Chem. 1]

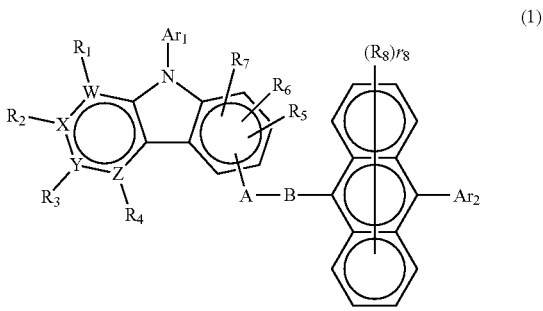

(1)

(in the formula, Ar$_1$ and Ar$_2$ may be the same or different from each other, wherein Ar$_1$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and Ar$_2$ represents a substituted or unsubstituted aromatic hydrocarbon group or a substituted or unsubstituted condensed polycyclic aromatic group; A and B may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_1$ to $R_7$ may be the same or different from one another, and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_8$ represents a deuterium atom, a fluorine atom, a chlorine atom, a cyano group, a trifluoromethyl group, or a linear or branched alkyl group having from 1 to 6 carbon atoms; $r_8$ represents 0 or an integer of from 1 to 8, wherein when $r_8$ is 2 or more, two or more of $R_8$'s may be the same or different from one another and when $r_8$ is 0, it means no substitution with $R_8$; and each of W, X, Y and Z represents a carbon atom or a nitrogen atom, wherein only one of W, X, Y and Z is nitrogen atom and the nitrogen atom in that case does not have the hydrogen atom or substituent group of $R_1$ to $R_4$); and

[Chem. 2]

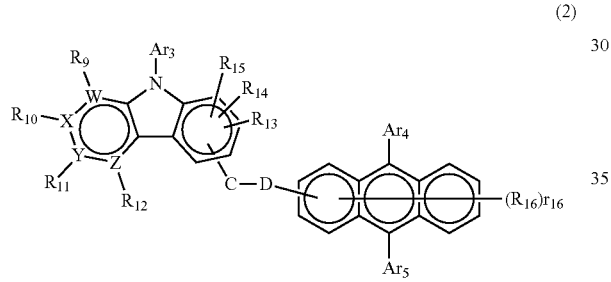

(2)

(in the formula, $Ar_3$, $Ar_4$ and $Ar_5$ may be the same or different from one another, wherein $Ar_3$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and each of $Ar_4$ and $Ar_5$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_9$ to $R_{15}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{16}$ represents a deuterium atom, a fluorine atom, a chlorine atom, a cyano group, a trifluoromethyl group or a linear or branched alkyl group having from 1 to 6 carbon atoms; $r_{16}$ represents 0 or an integer of from 1 to 7, wherein when $r_{16}$ is 2 or more, two or more of $R_{16}$'s may be the same or different from one another and when $r_{16}$ is 0, it means no substitution with $R_{16}$; and each of W, X, Y and Z represents a carbon atom or a nitrogen atom, wherein only one of W, X, Y and Z is nitrogen atom and the nitrogen atom in that case does not have the hydrogen atom or substituent group of $R_9$ to $R_{12}$).

2. The compound having a substituted anthracene ring structure and a pyridoindole ring structure according to claim 1, which is represented by the following general formula (3):

[Chem. 3]

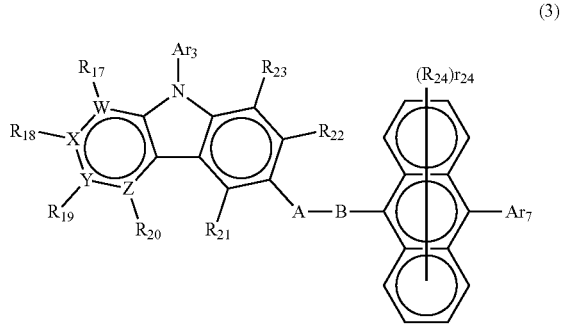

(3)

(in the formula, $Ar_6$ and $Ar_7$ may be the same or different from each other, wherein $Ar_6$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and $Ar_7$ represents a substituted or unsubstituted aromatic hydrocarbon group or a substituted or unsubstituted condensed polycyclic aromatic group; A and B may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{17}$ to $R_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{24}$ represents a deuterium atom, a fluorine atom, a chlorine atom, a cyano group, a trifluoromethyl group or a linear or branched alkyl group having from 1 to 6 carbon atoms; $r_{24}$ represents 0 or an integer of from 1 to 8, wherein when $r_{24}$ is 2 or more, two or more of $R_{24}$'s may be the same or different from one another and when $r_{24}$ is 0, it means no substitution with $R_{24}$; and each of W, X, Y and Z represents a carbon atom or a nitrogen atom, wherein only one of W, X, Y and Z is nitrogen atom and the nitrogen atom in that case does not have the hydrogen atom or substituent group of $R_{17}$ to $R_{20}$).

3. The compound having a substituted anthracene ring structure and a pyridoindole ring structure according to claim 1, which is represented by the following general formula (4):

[Chem. 4]

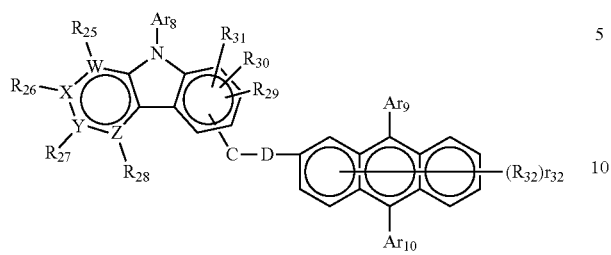

(4)

(in the formula, $Ar_8$, $Ar_9$ and $Ar_{10}$ may be the same or different from one another, wherein $Ar_8$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and each of $Ar_9$ and $Ar_{10}$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{25}$ to $R_{31}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{32}$ represents a deuterium atom, a fluorine atom, a chlorine atom, a cyano group, a trifluoromethyl group or a linear or branched alkyl group having from 1 to 6 carbon atoms; $r_{32}$ represents 0 or an integer of from 1 to 7, wherein when $r_{32}$ is 2 or more, two or more of $R_{32}$'s may be the same or different from one another and when $r_{32}$ is 0, it means no substitution with $R_{32}$; and each of W, X, Y and Z represents a carbon atom or a nitrogen atom, wherein only one of W, X, Y and Z is nitrogen atom and the nitrogen atom in that case does not have the hydrogen atom or substituent group of $R_{25}$ to $R_{28}$).

4. The compound having a substituted anthracene ring structure and a pyridoindole ring structure according to claim 1, which is represented by the following general formula (5):

[Chem. 5]

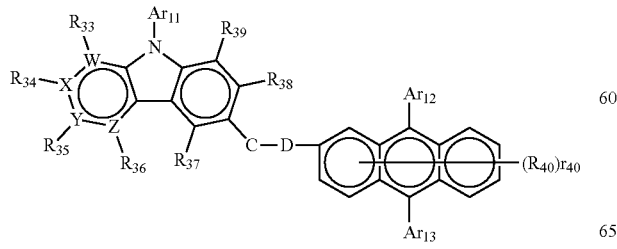

(5)

(in the formula, $Ar_{11}$, $Ar_{12}$ and $Ar_{13}$ may be the same or different from one another, wherein $Ar_{11}$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and each of $Ar_{12}$ and $Ar_{13}$ represents a substituted or unsubstituted aromatic hydrocarbon group or a substituted or unsubstituted condensed polycyclic aromatic group; C and D may be the same or different from each other and each represents a single bond, a substituted or unsubstituted aromatic hydrocarbon divalent group, a substituted or unsubstituted aromatic heterocyclic divalent group or a substituted or unsubstituted condensed polycyclic aromatic divalent group; $R_{33}$ to $R_{39}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; $R_{40}$ represents a deuterium atom, a fluorine atom, a chlorine atom, a cyano group, a trifluoromethyl group or a linear or branched alkyl group having from 1 to 6 carbon atoms; $r_{40}$ represents 0 or an integer of from 1 to 7, wherein when $r_{40}$ is 2 or more, two or more of $R_{40}$'s may be the same or different from one another and when $r_{40}$ is 0, it means no substitution with $R_{40}$; and each of W, X, Y and Z represents a carbon atom or a nitrogen atom, wherein only one of W, X, Y and Z is nitrogen atom and the nitrogen atom in that case does not have the hydrogen atom or substituent group of $R_{33}$ to $R_{36}$).

5. The compound having a substituted anthracene ring structure and a pyridoindole ring structure according to claim 2, wherein each of A and B in the aforementioned general formula (3) is a single bond.

6. The compound having a substituted anthracene ring structure and a pyridoindole ring structure according to claim 5, which is represented by the following general formula (3'):

[Chem. 6]

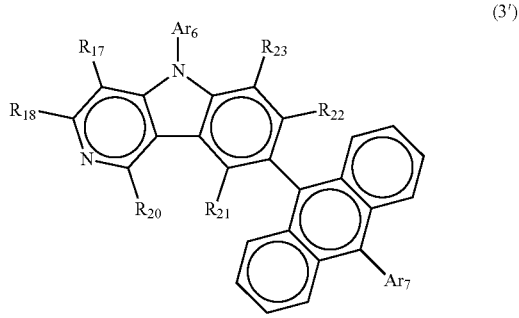

(3')

(in the formula, $Ar_6$ and $Ar_7$ may be the same or different from each other, wherein $Ar_6$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and Ar$_7$ represents a substituted or unsubstituted aromatic hydrocarbon group or a substituted or unsubstituted condensed polycyclic aromatic group; and R$_{17}$, R$_{18}$ and R$_{20}$ to R$_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

7. The compound having a substituted anthracene ring structure and a pyridoindole ring structure according to claim 2, which is represented by the following general formula (3"):

[Chem. 7]

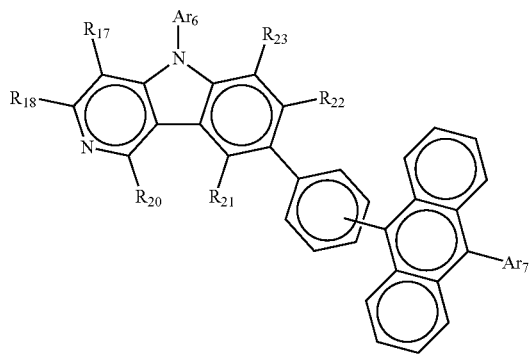

(3")

(in the formula, Ar$_6$ and Ar$_7$ may be the same or different from each other, wherein Ar$_6$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and Ar$_7$ represents a substituted or unsubstituted aromatic hydrocarbon group or a substituted or unsubstituted condensed polycyclic aromatic group; and R$_{17}$, R$_{18}$ and R$_{20}$ to R$_{23}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

8. The compound having a substituted anthracene ring structure and a pyridoindole ring structure according to claim 4, wherein each of C and D in the aforementioned general formula (5) is a single bond.

9. The compound having a substituted anthracene ring structure and a pyridoindole ring structure according to claim 8, which is represented by the following general formula (5'):

[Chem. 8]

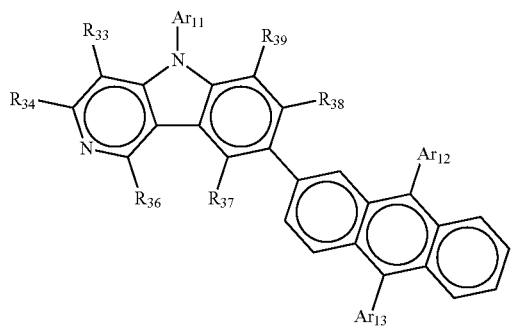

(5')

(in the formula, Ar$_{11}$, Ar$_{12}$ and Ar$_{13}$ may be the same or different from one another, wherein Ar$_{11}$ represents a substituted or unsubstituted aromatic hydrocarbon group having 5 to 18 carbon atoms, a substituted or unsubstituted aromatic heterocyclic group or a substituted or unsubstituted condensed polycyclic aromatic group, and each of Ar$_{12}$ and Ar$_{13}$ represents a substituted or unsubstituted aromatic hydrocarbon group or a substituted or unsubstituted condensed polycyclic aromatic group; and R$_{33}$, R$_{34}$ and R$_{36}$ to R$_{39}$ may be the same or different from one another and each represents a hydrogen atom, a deuterium atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group).

10. An organic electroluminescent device having a pair of electrodes and at least one organic layer interposed therebetween, wherein the aforementioned at least one organic layer contains the compound having a substituted anthracene ring structure and a pyridoindole ring structure, which is represented by the general formula (1) or the general formula (2) according to claim 1.

11. The organic electroluminescent device according to claim 10, wherein the aforementioned at least one organic layer contains an electron-transport layer, and the compound represented by the general formula (1) or the general formula (2) is present in the electron-transport layer.

12. The organic electroluminescent device according to claim 10, wherein the aforementioned at least one organic layer contains a hole-blocking layer, and the compound represented by the general formula (1) or the general formula (2) is present in the hole-blocking layer.

13. The organic electroluminescent device according to claim 10, wherein the aforementioned at least one organic layer contains a light-emitting layer, and the compound represented by the general formula (1) or the general formula (2) is present in the light-emitting layer.

14. The organic electroluminescent device according to claim 10, wherein the aforementioned at least one organic layer contains an electron-injection layer, and the compound represented by the general formula (1) or the general formula (2) is present in the electron-injection layer.

* * * * *